US012087446B2

(12) United States Patent
Kollada et al.

(10) Patent No.: US 12,087,446 B2
(45) Date of Patent: Sep. 10, 2024

(54) MULTIMODAL DYNAMIC ATTENTION FUSION

(71) Applicant: NEUMORA THERAPEUTICS, INC., Brisbane, CA (US)

(72) Inventors: Matthew Kollada, Deerfield, IL (US); Tathagata Banerjee, Walnut Creek, CA (US)

(73) Assignee: NEUMORA THERAPEUTICS, INC., Brisbane, CA (US)

( * ) Notice: Subject to any disclaimer, the term of this patent is extended or adjusted under 35 U.S.C. 154(b) by 0 days.

(21) Appl. No.: 17/740,713

(22) Filed: May 10, 2022

(65) Prior Publication Data

US 2022/0392637 A1 Dec. 8, 2022

Related U.S. Application Data

(60) Provisional application No. 63/196,047, filed on Jun. 2, 2021, provisional application No. 63/196,067, filed on Jun. 2, 2021.

(51) Int. Cl.
*G16H 50/20* (2018.01)
*A61B 5/00* (2006.01)
*A61B 5/0205* (2006.01)
*A61B 5/16* (2006.01)
*G06N 20/00* (2019.01)
*G16H 10/20* (2018.01)

(52) U.S. Cl.
CPC .......... *G16H 50/20* (2018.01); *A61B 5/0205* (2013.01); *A61B 5/165* (2013.01); *A61B 5/7264* (2013.01); *G06N 20/00* (2019.01); *G16H 10/20* (2018.01)

(58) Field of Classification Search
None
See application file for complete search history.

(56) References Cited

U.S. PATENT DOCUMENTS

| 2008/0254421 | A1  | 10/2008 | Warren |
| 2015/0005590 | A1  | 1/2015  | Libbus |
| 2017/0112427 | A1  | 4/2017  | Simon  |
| 2018/0143966 | A1  | 5/2018  | Lu     |
| 2019/0113973 | A1* | 4/2019  | Coleman ................. G06F 3/011 |

(Continued)

FOREIGN PATENT DOCUMENTS

| WO | WO-2019171049 A1 * | 9/2019 | ............. A61B 5/165 |
| WO | WO 2020/047253 A1  | 3/2020 |          |

(Continued)

OTHER PUBLICATIONS

Qureshi et al. (The Verbal and Non-Verbal Signals of Depression—Combining Acoustics, Text and Visuals for Estimating Depression Level) https://arxiv.org/pdf/1904.07656.pdf. Apr. 2019 (Year: 2019).*

(Continued)

*Primary Examiner* — Jonathan Ng
(74) *Attorney, Agent, or Firm* — NIXON PEABODY LLP

(57) ABSTRACT

Methods and systems are provided for diagnosing mental health conditions using multiple data modalities. In particular, a trained machine learning model is used for mental health diagnosis, wherein the trained model utilizes a dynamic fusion approach for capturing and preserving interactions as well as timing information between the multiple data modalities.

26 Claims, 15 Drawing Sheets

(56) References Cited

U.S. PATENT DOCUMENTS

| | | | |
|---|---|---|---|
| 2020/0121236 A1* | 4/2020 | Gao | G16H 10/60 |
| 2021/0319897 A1* | 10/2021 | Howard | G16H 10/60 |
| 2021/0358594 A1* | 11/2021 | Mellem | A61B 5/055 |
| 2022/0328064 A1* | 10/2022 | Shriberg | G10L 25/66 |
| 2022/0392637 A1* | 12/2022 | Kollada | A61B 5/7264 |

FOREIGN PATENT DOCUMENTS

| | | |
|---|---|---|
| WO | WO 2021/081418 A1 | 4/2021 |
| WO | WO 2022/232382 A1 | 11/2022 |

OTHER PUBLICATIONS

International Search Report and Written Opinion in International Application No. PCT/US2022/026714, mailed Jun. 29, 2022 (12 pages).

Garcia-Ceja et al. "Mental health monitoring with multimodal sensing and machine learning: A survey." Pervasive and Mobile Computing 51 (2018): pp. 1-26, Sep. 19, 2018 [retrieved Dec. 6, 2022 from the internet] https://www.sciencedirect.com/science/article/pii/S1574119217305692.

Zadeh et al. "Tensor fusion network for multimodal sentiment analysis." arXiv preprint arXiv:1707.07250 (2017), 12 pp., Jul. 23, 2017 [retrieved Dec. 6, 2022 from the internet] <https://arxiv.org/abs/1707.07250>.

Lu et al. "Multimodal and Multiscale Deep Neural Networks for the Early Diagnosis of Alzheimer's Disease using structural MR and FDG-PET images." Scientific Reports 8.1 (2018): pp. 1-13; Apr. 9, 2018 [retrieved Dec. 6, 2022 from the internet] https://www.nature.com/articles/s41598-018-22871-z.

Strawbridge R., "Multimodal Markers and Biomarkers of Treatment." Psychiatric Times, 35(7), (2018), 10 pp., Jul. 31, 2018.

International Search Report and Written Opinion in International Application No. PCT/US2022/030507, mailed Aug. 25, 2022 (11 pages).

Quershi et al., The Verbal and Non Verbal Signals of Depression—Combining Acoustics, Text and Visuals for Estimating Depression Level; Apr. 2, 2019; 11 pp. [retrieved Jul. 26, 2022] Retrieved from the internet <URL: https://arxiv.org/pdf/1904.07656.pdf>.

\* cited by examiner

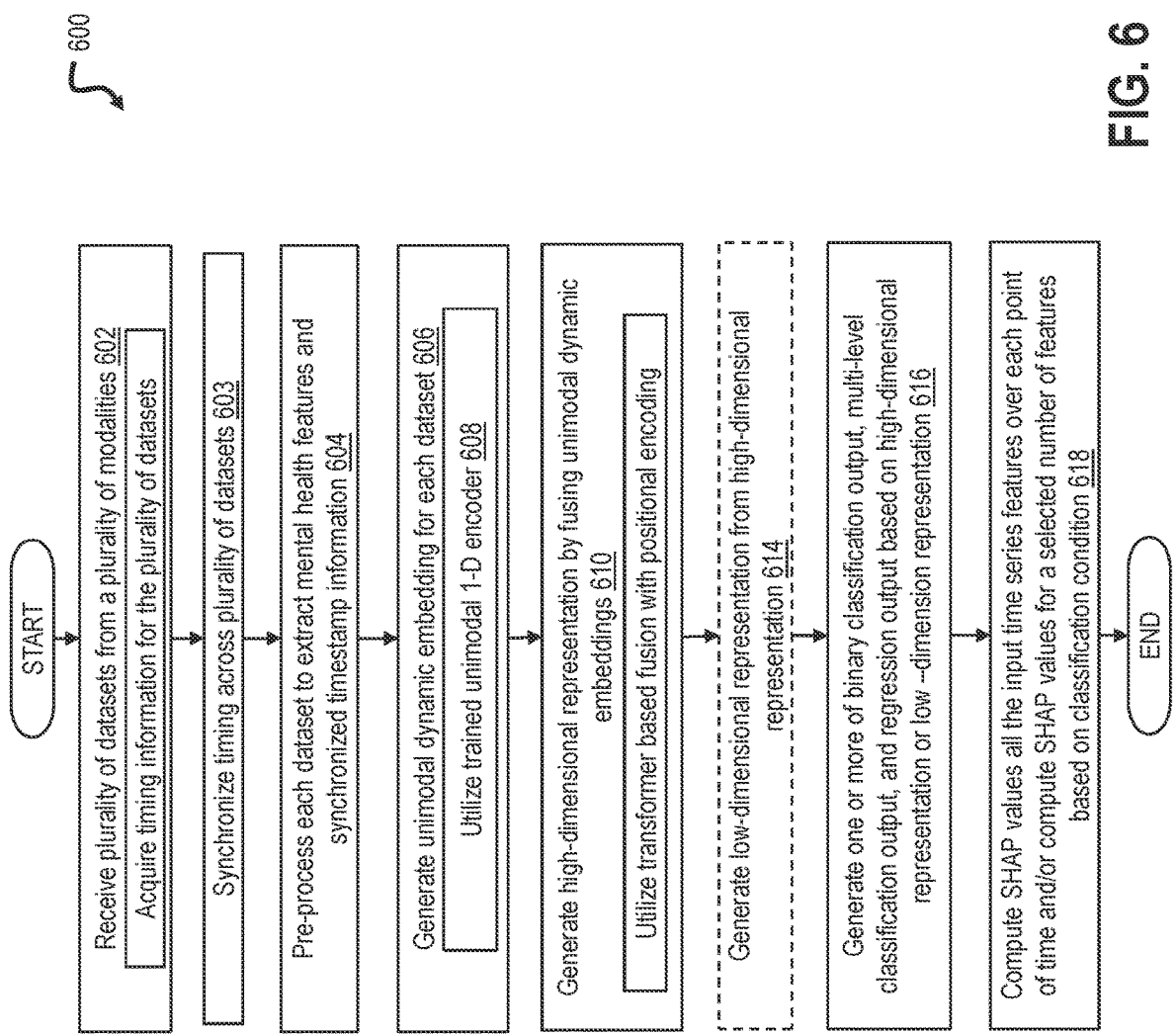

| PHQ-9 | GAD-7 | SHAPS |
|---|---|---|
| AU16: Lower Lip Depressor | Polarity | Polarity |
| Valence | Short-Time Fourier Transform Energy Spectrogram 9 | Subjectivity |
| Dominance | Chroma Energy Normalized Spectrogram 11 | |
| Subjectivity Polarity | Valence Shimmer | AU10: Upper Lip Raiser |
| Arousal | MFCC 8 | MFCC 1 Spectral Spread |
| MFCC 10 | Contrast Spectrogram 3 | Proper Noun Tag Logarithmic Energy |
| # of Characters | MFCC 1 | Singular Noun Tag |
| Coordinating Conjunction Tag | AU16: Lower Lip Depressor | Contrast Spectrogram 6 |
| Contrast Spectrogram 5 | # of Characters | Chroma Energy Normalized Spectrogram 4 |
| Audio | Video | Text |

FIG. 9B

MULTIMODAL DYNAMIC ATTENTION FUSION

CROSS REFERENCE TO RELATED APPLICATIONS

This application claims priority to U.S. Provisional Application No. 63/196,047 filed Jun. 2, 2021 titled INTERPRETABLE DEEP MULTIMODAL FUSION, and U.S. Provisional Application No. 63/196,067 filed Jun. 2, 2021 titled MULTIMODAL DYNAMIC ATTENTION FUSION, the contents of all of which are incorporated herein by reference.

FIELD

The present invention is directed to processing data from multiple modalities for mental health evaluation.

BACKGROUND

The following description includes information that may be useful in understanding the present invention. It is not an admission that any of the information provided herein is prior art or relevant to the presently claimed invention, or that any publication specifically or implicitly referenced is prior art.

Mental health conditions, such as mood disorders are common and debilitating, and can present across multiple related symptom axes, including depressive, anxious, and anhedonia symptoms. Current approaches to mental health evaluation rely primarily on assessment by a healthcare provider. As such, accuracy of diagnosis may vary depending on experience, expertise, and/or physical and mental fatigue, among other factors. Further, other approaches largely focus on single modality processing to assist in mental health evaluation, including data preprocessing, machine learning, and diagnostic outputs based on unimodal inputs.

SUMMARY

The disclosed technology is directed to improvements in multimodal and multi-sensor diagnostic devices, that utilize machine learning algorithms to diagnose patients based on data from different sensor types and formats. Current machine learning algorithms that classify a patient's diagnosis focus on one modality of data output from one type of sensor or device. This is because, among other reasons, it is difficult determine which modalities or features from different modalities will be most important to a diagnosis, and also very difficult to identify an algorithm that can effectively to combine them to diagnose health disorders.

This difficulty is particularly acute in the mental health space, as mental health disorders are expressed as complex phenotypes of a constellation of symptoms that may be expressed through a patient's speech, facial expressions, posture, brain activity (e.g. EEG, MRI), cardiac activity, genotype, phenotype, proteomic expression, inflammatory marker levels, and others.

Recognizing that mood disorder symptoms may manifest in patient facial expressions and speech, the inventors herein have identified that by modeling audio, video and text data, for example using remotely collected videos, mental health symptoms may be characterized by implementing machine learning methods that are (1) multimodal: successful in integrating information from different modalities (2) interpretable: can be validated by clinicians and scientists (3) robust: can handle data that is collected through methods that scale (e.g. remote collection) and (4) transdiagnostic: successful in identifying symptoms in different mood disorders.

An example machine learning approach for detecting depression is provided by Al Hanai et al in *Detecting Depression with Audio/Text Sequence Modeling of Interviews. Proc. Interspeech* 2018, 1716-1720. Therein, utilizing data from individuals undergoing depression screening, interactions between audio and text sequences are modeled in a Long Short Term Memory (LSTM) neural network model to detect depression.

However, there are several disadvantages with the above-mentioned approach and other previous depression detection approaches. As an example, the above-mentioned audio-text interaction method relies on fusing static embeddings, which don't integrate temporal information across modalities, thereby inhibiting performance. Further, there has not been much focus on model interpretability such as feature importance which can help clinicians validate such methods and provide pathways for digital marker discovery. Furthermore, the data used in the above-mentioned approach and other previous machine learning based approaches has been collected in clinical or laboratory settings, thus limiting adoption to more scalable, but potentially noisier data collection methods. Further still, previous approaches, including the approach by Al Hanai et al, have focused only on symptoms of depression. However, mood disorders may consist of other co-morbid illnesses such as anxiety and/or anhedonia.

The inventors herein have developed a multimodal machine learning method to identify symptoms of mood disorders using multimodal data, including audio, video, and text data.

In one example, a method for mental health evaluation comprises: processing, via a modality processing logic, a plurality of datasets from at least two types of sensors to output a set of dynamic data representations for each of the at least two types of sensors, wherein each of the set of dynamic data representations comprises a vector comprising a set of features including time domain information from each of the at least two types of sensors; processing, via a fusion layer, the set of data representations from each of the at least two types of sensors to output a combined data representation, the combined data representation including the time domain information; processing the combined data representation, via a relevance determination logic, the relevance of the combined data representation to a health diagnosis; and determining, via a diagnosis determination logic, a mental health diagnosis based on the relevance of the combined data representation.

In this way, the method for mental health evaluation takes into account dependencies across modalities within a temporal context by learning dynamic (i.e. temporal) embeddings for each modality. Further, the dynamic embeddings are combined through a multimodal fusion model, such as a transformer-based model. This framework provides improved performance compared to previous approaches that employ static (i.e. non-temporal) unimodal embeddings and/or use fewer modalities.

In one example, a multimodal neural network model for extracting the dynamic embeddings and fusing the dynamic embedding is trained using a novel dataset. The dataset includes audio, video, and text data collected remotely through consumer smartphones without clinical supervision. In some examples robust quality control methods may be implemented to reduce potential variability. Further, the dataset may include responses to one or more questionnaires for multiple mood disorder symptoms including depression, anxiety, and anhedonia.

In one embodiment, a model explanation logic may be used to identify and output the most important features in these models. An example model explanation logic may use SHapley Additive exPlanations (SHAP) to identify the most important features. The features identified via the model explanation logic may enable clinicians to find salient portions of the video from larger clips to review the diagnosis, which improved clinician confidence. Further, the feature identified via the model explanation logic facilitates identification and isolation of subsets of text, audio, and/or video data for a given patient, and evaluate the impact of one or more of words, facial, and/or vocal expression to the diagnosis. These audio, video, and text subsets may be used track symptom and/or mental health condition improvement over time. Further still, the audio, video, and text subsets may be used for customized monitoring and treatment of the mental health conditions.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIG. 6 is a flow chart illustrating an example method for performing mental health evaluation using a trained dynamic fusion model, according to an embodiment of the disclosure.

FIG. 9B shows a plurality of important features determined based on SHAP for each classification.

Figure 1A:
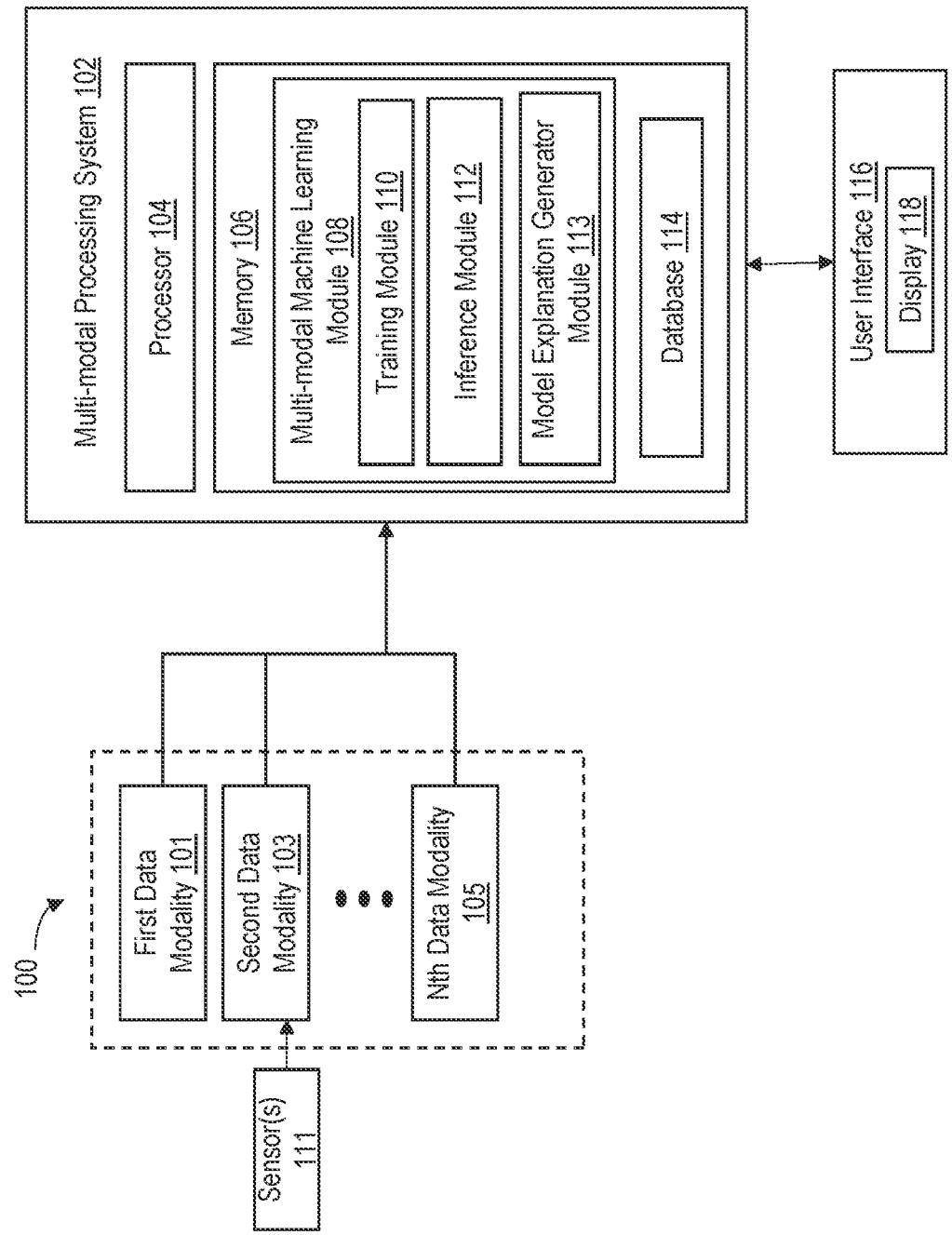
FIG. 1A is a block diagram of a multimodal processing system for implementing a multimodal dynamic fusion model for mental health evaluation, according to an embodiment of the disclosure.

In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced.

DETAILED DESCRIPTION

One skilled in the art will recognize many methods and materials similar or equivalent to those described herein, which could be used in the practice of the present invention. Indeed, the present invention is in no way limited to the methods and materials specifically described.

In some embodiments, properties such as dimensions, shapes, relative positions, and so forth, used to describe and claim certain embodiments of the invention are to be understood as being modified by the term "about."

Definitions

As used herein, the term "patient" refers to a person or an individual undergoing evaluation for a health condition and/or undergoing medical treatment and/or care.

As used herein, the term "data modality" or "modality data" refers to representative form or format of data that can be processed and that may be output form a particular type of sensor or processed, manipulated, or captured by a sensor in a particular way, and may capture a particular digital representation of a particular aspect of a patient or other target. For example, video data represents one data modality, while audio data represents another data modality. In some examples, three dimensional video represents one data modality, and two dimensional video represents another data modality.

As used herein, the term "sensor" refers to any device for capturing a data modality. The term "sensor type" may refer to different hardware, software, processing, collection, configuration, or other aspects of a sensor that may change the format/type/and digital representation of data output from the sensor. Examples of sensors/types include camera, two dimensional camera, microphone, audio sensors, three dimensional camera, keyboard, user interface, touchscreen, microphone, electrocardiograph (ECG) sensors, electroencephalography (EEG) sensors, electromyography (EMG) sensors, respiratory sensors, and medical imaging systems including, but not limited to functional magnetic resonance imaging (fMRI), T1-weighted MRI, and diffusion weighted MRI.

As used herein, the term "mental health" refers to an individual's psychological, emotional, cognitive, or behavioral state or a combination thereof.

As used herein, the term "mental health condition" refers to a disorder affecting the mental health of an individual, and the term "mental health conditions" collectively refers to a wide range of disorders affecting the mental health of an individual. These include, but not limited to clinical depression, anxiety disorder, bipolar disorder, dementia, attention-deficit/hyperactivity disorder, schizophrenia, obsessive compulsive disorder, autism, post-traumatic stress disorder, anhedonia, and anxious distress.

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations may be depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Overview

The present description relates to systems and methods for mental health evaluation using multiple data modalities. In particular, systems and methods are provided for combining multiple data modalities through a multimodal dynamic fusion model that effectively incorporates indications of mental health from each modality as well as multi-level interactions (e.g., bimodal, trimodal, quadmodal, etc.) between the data modalities.

For instance, in some examples, data modality processing includes a step of producing a fusion of each of the features of each of the modalities (or particular subsets), in order to output a new set of features that account for complimentary interactions between particular features of particular modalities. Accordingly, this produces combined features that will have a higher impact on the classification if both the underlying original features are present or higher.

Further, temporal context of the features is maintained when generating the feature embedding for each of the data modalities by utilizing a dynamic unimodal encoder. The feature embeddings that include temporal information or temporal context are dynamic feature embeddings. Subsequently, the temporal context is integrated during fusion of the dynamic feature embeddings by applying positional encoding in a transformer-based fusion method. For example, facial expression change and vocal inflection while a salient word is uttered is captured by maintaining temporal information or temporal context of the features from each modality before fusion (that is, when generating feature embeddings) and during fusion.

In this way, information across modalities are integrated within a temporal context through dynamic embeddings to form a multimodal sequence and efficiently process this sequence using the transformer. As a result, classification performance of the multimodal dynamic fusion model is significantly improved. This is very advantageous for diagnosing mental health disorders, because they are exhibited as a complex constellation of symptoms, that are not captured by systems that process modality by modality or by approaches that do not obtain and/or maintain the temporal information.

The technical advantages of the dynamic fusion model include improved accuracy in mental health evaluation, which is evidenced by significant improvement in classification performance of the dynamic fusion model. Particularly, by obtaining and maintaining temporal information of the mental health features from a plurality of modalities, interaction between the different modalities is captured efficiently and more accurately in resulting high dimensional representation (that is, in the multimodal fused dynamic embedding obtained after fusion), which also includes individual unimodal contributions. For instance, complementary effects between two or more modalities are all captured in a temporal context when using dynamic fusion. When the high dimensional representation is input into one or more classifiers for mental health, the output mental health classification is generated by taking into account the interactions between the different modality data as well timing of the interactions. For example, biomarkers of mental health from a video modality (e.g., facial expression) combined with evidence of vocal manifestations (e.g., tone) and/or utterance (e.g., uttering a salient word) extracted from one or more of audio and language modalities and the timing of the detection of the video, audio, and language biomarkers increases accuracy of mental health evaluation by the dynamic fusion model.

Further, the speed of mental health evaluation and processing is improved by utilizing the dynamic fusion model for mental health evaluation. Specifically, due to the combination of the features from the various modalities generated in the high dimensional representation of the dynamic fusion model, an amount of data required to evaluate mental health symptoms is reduced. Current approaches, whether manual or partly relying on algorithms, are time consuming requiring patient monitoring for a long duration over each assessment session. Even then, the interactions between multiple data modalities are not captured effectively. In contrast, using the dynamic fusion model, mental health evaluation may be performed with shorter monitoring times (e.g., around 5 minutes for each session) since the high dimensional representation provides additional information regarding feature interactions and the timing of the feature interactions among the modalities that allows for faster mental health evaluation. For example, for each data modality, an amount of data acquired for evaluation may be less, which reduces the duration for data acquisition as well as improves analysis speed. In this way, the dynamic fusion model provides significant improvement in mental health analysis, in terms of accuracy as well as speed.

Further, the dynamic fusion model enables short-term and long term mental health progression monitoring. Due to the improvement in speed and classification performance of the dynamic fusion model, mental health progression may be more efficiently and continuously monitored over short-term as well as long-term intervals. For example, a patient response to a treatment (e.g., drug treatment, counseling, etc.) may be more closely monitored. As a result, when necessary, adjustments to the treatments may be prescribed based on the mental health progression monitored using the dynamic fusion model. As a non-limiting example, a clinician may instruct a patient to take a video recording at one or more time points after prescribed drug intake. The video recording may include vocal expression activities, where user is asked to record videos of their faces while responding to prompts (e.g., generated via a mental health evaluation app on a smart phone). Thus, the video recording may acquire video, audio, and language data, which may be processed in a time-dependent manner via the dynamic fusion model. That is, the interactions between facial, voice, and/or language features as well as timing of interactions are captured and processed via the dynamic fusion model. The clinician may then remotely monitor the mental health evaluation output by the dynamic fusion model, and if necessary, make desired adjustments to the treatment (e.g., increase dosage). Further, in some examples, the dynamic fusion model may be used for long-term mental health monitoring (e.g., as a part of annual health check-up, to evaluate mental health progression after prescribed long-term activity (exercise, counseling, etc.)). Furthermore, the dynamic fusion model may be useful for post-partum depression monitoring and mental health evaluation.

In some examples, a severity scale of each mental health classification outcome may be generated. For example, responsive to determining a depression outcome, a severity of the depression outcome (e.g., mild, moderate, severe, or any clinical scale) may be determined.

Figure 10:
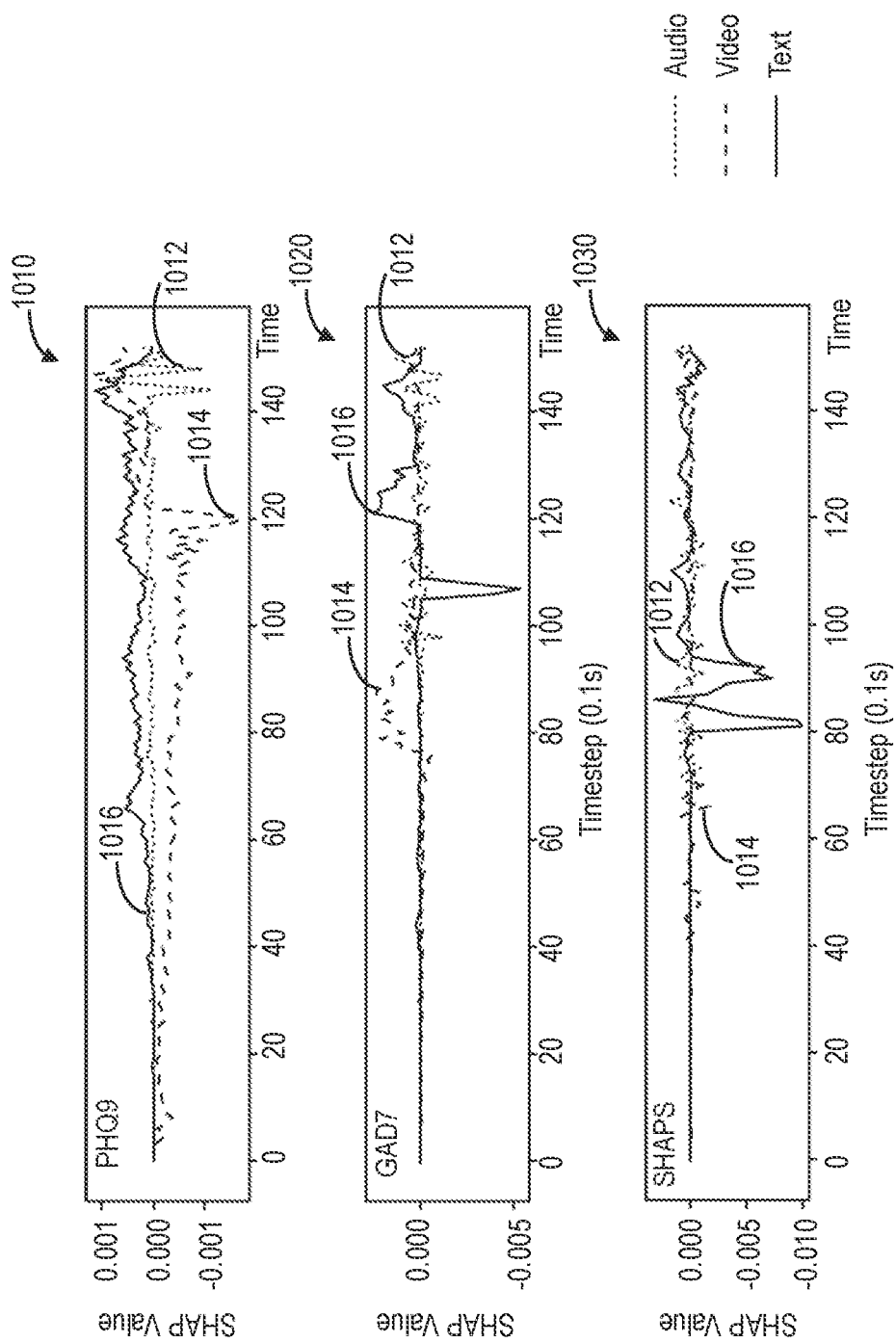
FIG. 10 shows SHAP values over time for an input time series data.

Further, a model explanation technique, such as a SHAP-based interpretability method, is utilized to determine a set of important features based on which a given mental health classification is generated. The SHAP-based interpretability method enables computation of the SHAP values for all the input features (which are time series features) over each point of time. Thus, an additional level of information for the feature importance is obtained. For example, clinicians could use these type of data to isolate the impacts of specific words, facial or vocal expressions, or to find particularly salient portions of the video in larger clips. An example time series SHAP values of one participant for the top audio, video and text features for each of the scales is shown in FIG. 10.

System

FIG. 1A shows a mental health processing system 102 that may be implemented for multimodal mental health evaluation. In one embodiment, the mental health processing system 102 may be incorporated into a computing device, such as a workstation at a health care facility. The mental health processing system 102 is communicatively coupled to a plurality of sensors and/or systems generating a plurality of data modalities 100, such as a first data modality 101, a second data modality 103, and so on up to Nth data modality 105, where N is a real number. It will be appreciated that any number of data modalities may be utilized for mental health evaluation. The mental health processing system 102 may receive data from each of the plurality of sensors and/or systems 111. The plurality of sensors and systems 111 may include wearable devices that capture one or more physiological information and behavioral information simultaneously. In one example, when data from at least two sensors are acquired, the data from the at least two sensors may be acquired simultaneously. In another example, when at least two data modalities are obtained (e.g., video data, audio data, utterance (that is, text/language data from speech to text conversion)), the data modalities are acquired simultaneously. In the context of mental health evaluation, the inventors have identified that timing information of the features in each modality is crucial for capturing interaction between the different modalities for mental health evaluation. As such, the modality data is processed in such a way so as to preserve the timing information obtained during acquisition. In one example, as discussed further below features from the data modalities as well as timing information (which may be encoded as a time stamp, sine-cosine encoding, etc.) is captured and preserved until after fusion. In this way, the systems and methods described below provide improvement in mental health evaluation.

In one example, the mental health processing system 102 may receive data from a storage device which stores the data generated by these modalities. In another embodiment, the mental health processing system 102 may be disposed at a device (e.g., edge device, server, etc.) communicatively coupled to a computing system that may receive data from the plurality of sensors and/or systems, and transmit the plurality of data modalities to the device for further processing. The mental health processing system 102 includes a processor 104, a user interface 114, which may be a user input device, and display 116.

Figure 1B:
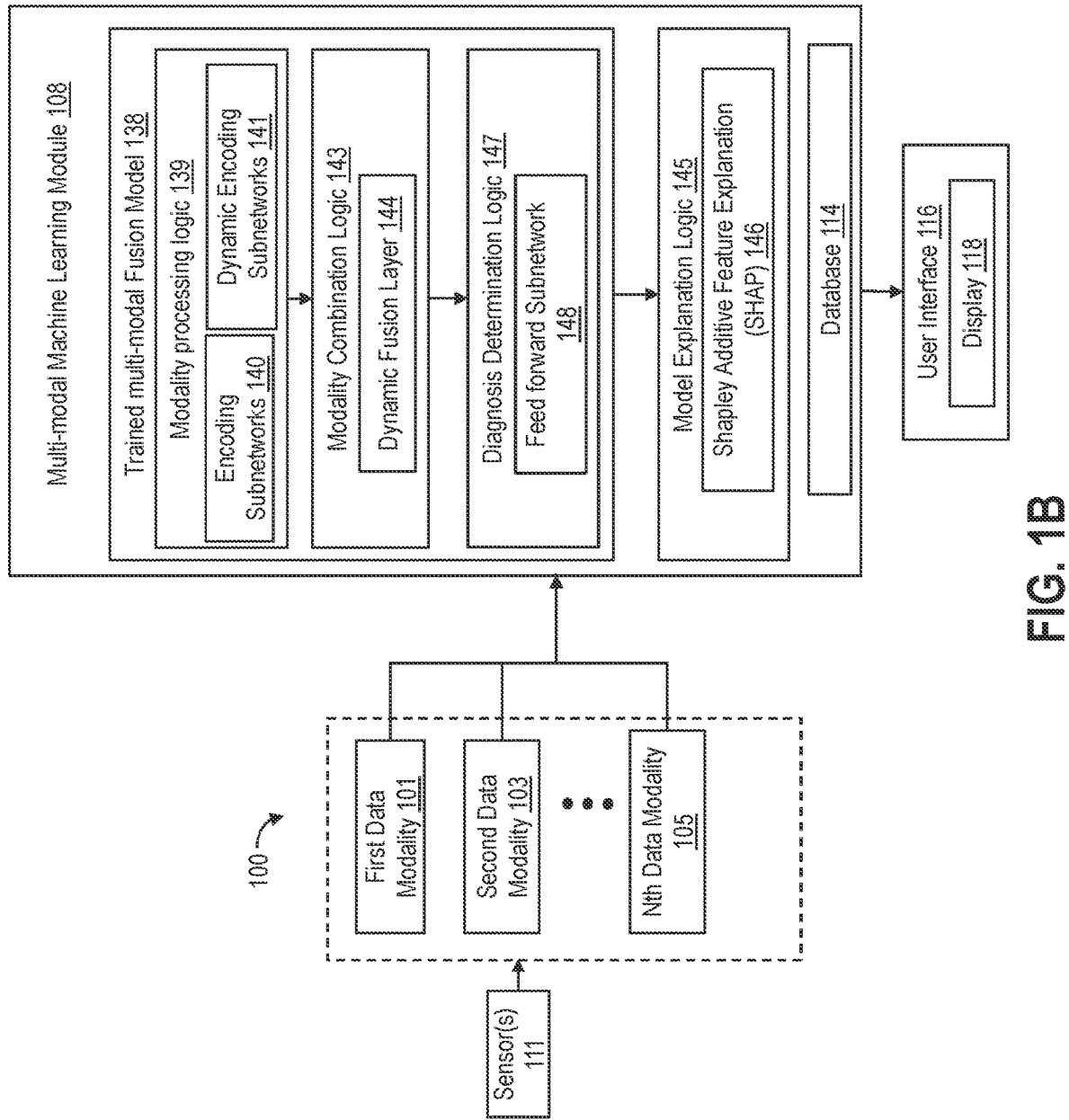
FIG. 1B is a block diagram of a trained multimodal dynamic fusion model implemented in the multimodal processing system of FIG. 1A, according to an embodiment of the disclosure.

Non-transitory memory 106 may store a multimodal machine learning module 108. The multimodal machine learning module 108 may include a multimodal dynamic fusion model that is trained for evaluating a mental health condition using input from the plurality of modalities 100. Components of the multimodal dynamic fusion model are shown at FIG. 1B. Accordingly, the multimodal machine learning module 108 may include instructions for receiving modality data from the plurality of sensors and/or systems, and implementing the multimodal dynamic fusion model for evaluating a mental health condition of a patient. An example server side implementation of the multimodal dynamic fusion model is discussed below at FIG. 2. Further, example architecture of the multimodal dynamic fusion model is described at FIG. 5.

Non-transitory memory 106 may further store training module 110, which includes instructions for training the multimodal dynamic fusion model stored in the machine learning module 108. Training module 110 may include instructions that, when executed by processor 104, cause mental health processing system 102 train one or more subnetworks in the dynamic fusion model. Example protocols implemented by the training module 110 may include learning techniques such as gradient descent algorithm, such that the dynamic fusion model can be trained and can classify input data that were not used for training.

Non-transitory memory 106 also stores an inference module 112 that comprises instructions for testing new data with the trained multimodal dynamic fusion model. Further, non-transitory memory 106 may store modality data 114 received from the plurality of sensors and/or systems. In some examples, the modality data 114 may include a plurality of training datasets for each of the one or more modalities 100.

Mental health processing system 102 may further include user interface 116. User interface may be a user input device, and may comprise one or more of a touchscreen, a keyboard, a mouse, a trackpad, a motion sensing camera, and other device configured to enable a user to interact with and manipulate data within the processing system 102.

Display 118 may be combined with processor 104, non-transitory memory 106, and/or user interface 116 in a shared enclosure, or may be peripheral display devices and may comprise a monitor, touchscreen, projector, or other display device known in the art, which may enable a user to view modality data, and/or interact with various data stored in non-transitory memory 106.

FIG. 1B depicts the components of the multimodal dynamic fusion model 138, according to an embodiment. The multimodal dynamic fusion model is also referred to herein as "multimodal fusion model". The various components of the multimodal fusion model 138 may be trained separately or jointly.

The multimodal fusion model 138 includes a modality processing logic 139 to process plurality of data modalities from the plurality of sensors 111 to output, for each of the plurality of data modalities, a data representation comprising a set of features. In one example, the modality processing logic 139 includes one or more encoding subnetworks 140, where each encoding subnetworks 140 is a set of instructions for extracting a set of features from each data modality.

Further, the multimodal fusion model 138 may include a synchronized time stamp acquisition logic (shown in FIG. 2) to obtain timing information from each of the plurality of data modalities and/or synchronize timing across the plurality of data modalities. Each encoding subnetwork 140 may be configured to extract the set of features from each data modality at a desired timing resolution. In one example the timing resolution may be 0.1 seconds. In other examples, the features from each data modality may be extracted at a timing resolution of less than 0.1 seconds. The features may be extracted at millisecond timing resolution or microsecond timing resolution, for example. In some examples, the features may be extracted at a timing resolution of greater than 0.1 seconds but equal to or less than one second. In various examples, the timing resolution may be 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1.0 second. In still further examples, the desired timing resolution may be 5 seconds or less than 5 seconds. Further, the timing information is preserved during feature extraction and across the plurality of data modalities. In one example, time stamps may be used for the extracted features. In some examples, encoding, such as sine-cosine encoding may be utilized in order to encode timing information with the set of features. In this way, timing information of the set of features is preserved and interaction between the different features from the different data modalities is more accurately learned in the subsequent multimodal representation. For instance, if the set of features were acquired from a set of sensors simultaneously, the timing or time stamp information would include information of how the different features related to each other based on the timing of capture and therefore their relevance to a diagnosis (for instance) based on their sequence in time. Accordingly, if the set of features are recorded simultaneously using a synchronized time stamp acquisition logic (FIG. 2), the time stamps for each feature could be related in time even if they are acquired by different sensors.

The modality processing logic 139 and other logic described herein can be embodied in a circuit or the modality processing logic 139 and other logic described herein can be executed by a data processing device such as the multimodal processing system 102. The subnetworks 140 may be based on the data modality from which feature extraction is performed. In one example, the subnetworks 140 may be a feed-forward neural network, a convolutional neural network, or a transformer or a combination thereof. In another example, the subnetworks may include one or more signal processing modules, such as framing and windowing, fourier transform, mel filter bank, and/or frequency wrapping, or other signal processing approaches for extracting features from the data acquired via the sensors 100. In some examples, the modality processing logic 139 may further comprise a set of modality preprocessing logic for pre-processing data modalities.

The multimodal fusion model 138 further includes one or more dynamic encoding subnetworks 141. For each modality, a dynamic encoding subnetwork receives the set of features (extracted from the input data from the sensor) and generates a corresponding unimodal dynamic embedding. The encoding subnetwork is a unimodal encoder. The encoding subnetwork comprises stacked convolution blocks (1D convolution layer followed by batch normalization and ReLU activation) which is configured to extracted dynamic embeddings from each of the individual modalities. In this way, the dynamic encoding subnetwork is a convolutional-based subnetwork, which preserves temporal information of the embeddings from the different modalities. The dynamic embeddings allows integration of information across modalities within a temporal context (e.g. facial expression change and vocal inflection while a salient word is uttered). An example unimodal dynamic encoder for generating a set of dynamic unimodal embeddings from an unimodal dataset is shown and described with respect to FIG. 3B.

The multimodal fusion model 138 further includes a modality combination logic 143 to process the data representations to output a combined data representation comprising multimodal high dimensional representation of each set of features. The modality combination logic 143 includes a dynamic fusion layer 144 including a set of instructions for generating a time-integrated high dimensional representation of the plurality of sets of features from the plurality of data modalities. Accordingly, the modality combination logic 143 includes a transformer-based fusion model, such as a Transformer encoder implementing a multi-head attention based mechanism to learn the multimodal representation for mental health classification.

Further, the dynamic fusion model 138 includes a diagnosis determination logic 147 to determine a mental health diagnosis based on the relevance of the products to the mental health diagnosis. The mental health diagnosis comprises at least one of: a psychiatric disorder, a depression, a schizophrenia, an anxiety, a panic disorder, a borderline personality disorder, an obsessive compulsive disorder, a post-traumatic stress disorder, an autism spectrum disorder, a mood disorder in epilepsy, a personality disorder, a cognitive change associated with chemotherapy, an attention deficient hyperactivity disorder (ADHD), a neurodevelopmental disorder, a neurodegenerative disorder, an Alzheimer's disease, or a dementia.

Figure 5A:
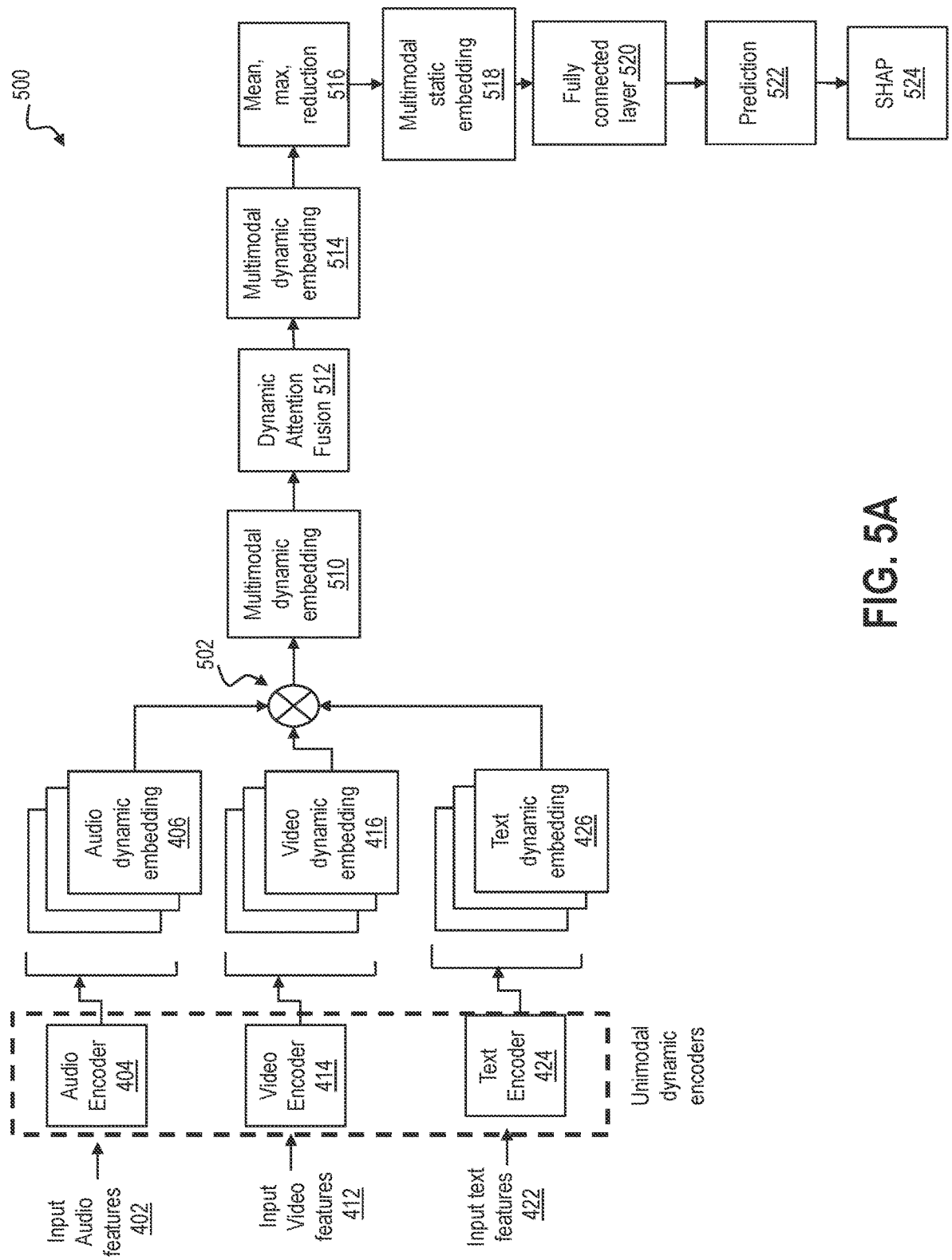
FIG. 5A is a schematic of a trained multimodal dynamic fusion model implemented for mental health evaluation using audio, video, and text modalities, according to an embodiment of the disclosure.

Example multimodal fusion model using audio, video and textual modalities as input, and performing three classifications to predict binary outcome labels related to the presence of symptoms of (1) depression (total PHQ-9 score >9), (2) anxiety (total GAD-7 score >9), and (3) anhedonia (total SHAPS score >25) is described at FIG. 5A. It will be appreciated that the multimodal fusion model can be trained to classify a variety of mental health conditions including but not limited to those mentioned above.

In one example, the diagnosis determination logic 147 comprises a supervised machine learning model, wherein the supervised machine learning model comprises a random forest, support vector machine, Bayesian Decision List, linear regression, logistic regression, naïve Bayes, linear discriminant analysis, decision tree, k-nearest neighbor, or neural network. In one example, the supervised machine learning model is trained using responses to clinical questionnaires as the outcome label.

The multimodal machine learning module comprises a model explanation logic 145. The model explanation logic 145 may include an interpretable model for explaining the dynamic fusion model 138. Interpretable models may be local or global. In one example, the model explanation logic may be configured to interpret and identify a number of important features based on which the trained dynamic fusion model 138 made a mental health prediction. In another example, the model explanation logic 145 may be utilized during training to fine-tune one or parameters of the dynamic fusion mode, such as a number of heads for multi-head attention, number of encoding units for the transformer, etc.

In one example, the important features contributing to a classification outcome of the dynamic fusion model 138 may be obtained by computing Shapley values based on a Shapley additive explanations (SHAP) technique. The SHAP technique implements a SHAP Gradient Explainer algorithm based on an Integrated Gradients algorithm. Applying additive feature attribution, a SHAP value for a given input variable can be approximated as the expectation of gradients that were computed for randomly generated input samples after adding Gaussian noise to each input for different base-lines/references. This allows calculation of SHAP values for each of our input variables for each subject and time point. The SHAP values may be summarized over the subjects and temporal axes, resulting in a global importance value for each feature. Other interpretable techniques, such as local interpretable model-agnostic explanations (LIME) may be used, and are within the scope of the disclosure.

Using SHAP values, features that are most responsible for a given outcome may be determined. In one example, SHAP values may be determined during training to determine one or more parameters for multimodal machine learning model, such as a minimal duration of video recording that may be needed to obtain desired performance. Other parameters such as a number of convolutional layers, a number of multi-head in an attention module, etc., may also be fine-tuned based on the SHAP values to obtain desired performance. Further still, in some examples, for each of the input features over time (that is for each time point at a desired time resolution), the SHAP values may be displayed in a graph over time. Thus, time points and the corresponding features that drove the diagnosis may be identified using SHAP. As a non-limiting example, during mental health evaluation, a patient may be asked to record a self-video while answering one or more questions and performing one or more tasks guided by a mental health evaluation application (e.g., an app on a computing device). The datasets (e.g., audio, video, and language data) may be acquired via the computing device and a mental health evaluation output is generated for one or more mental health conditions (e.g., depressed or not-depressed or a severity of depression). Along with the mental health output, for the input dataset, SHAP values may be generated over time using a SHAP model. In one example, the SHAP values may be displayed as a graph comprising plots for each data modality over time. In some other example, one or more selected features (e.g., features having a relevance or importance to a current mental health evaluation greater than a threshold relevance) and corresponding time points may be displayed along with the mental health output. For example, the mental health evaluation output and one or more SHAP-based indications may be provided. The one or more SHAP indications may include selected features contributing to the output and/or plots of SHAP scores for all input features for all input data modalities (with or without selected feature highlights) may be displayed to the clinician on a clinician user interface. Based on the SHAP indications, clinician may select a desired video clip for further evaluation, identify responses (by the patient) that drove the mental health evaluation by the machine learning model, and/or assign a confidence level to the output mental health condition. In some examples, the systems and methods may have features that automatically play portions of the data (e.g., video clip or audio clip) that had the highest threshold relevance to a mental health diagnosis. In some examples, portions of the video clip may include boxes, or other markings to identify features with the highest relevance (e.g. display the pixels relating to features of higher relevance brighter or in different color scales). In some examples, this could include display portions of data on a graph or otherwise that contributed most to the classification. For instance, for ECG data modality, portions of the ECG waveform could be boxed, highlighted, or otherwise marked to display the relevance to a clinician or caregiver.

In some examples, the SHAP values may be correlated with one or more questions and/or one or more tasks. For example, timing of questions and/or tasks may be correlated with the patient responses which in turn may be correlated with the audio, video, and text features over time. Thus, the questions and/or tasks may be correlated with the SHAP values of features over time. Accordingly, based on the SHAP values, timing of occurrence of one or more important features (e.g., having relevance based on SHAP value greater than threshold relevance) may be identified and based on the timing of occurrence of one or more important features, the corresponding questions and/or tasks that drove the identification of the important features may be determined. Thus, in one example, the relevant question and/or tasks that contributed to a given prediction may be identified and automatically displayed to the clinician.

In some examples, a degree of relevance of the features may be identified and indicated to the user. For example, based on the SHAP value computed, one or more subsets of features with different relevance degrees may be identified. As a non-limiting example, a first subset of features having a low relevance may be identified based on relevance at or below a first threshold; a second subset of features having a moderate relevance may be identified based on relevance above the first threshold and at or below a second higher threshold, and a third subset of features having a high relevance may be identified based on relevance above the second higher threshold. The different degrees of relevance may be indicated to the user with different relevance indications (e.g., different color highlights). For example, SHAP values for each modality may be represented as plots over time for the input features (e.g. FIG. 10). Features and corresponding time points having different degrees of relevance may be highlighted differently (e.g., yellow for low relevance, orange for medium relevance, red for high relevance etc.)

Figure 2:
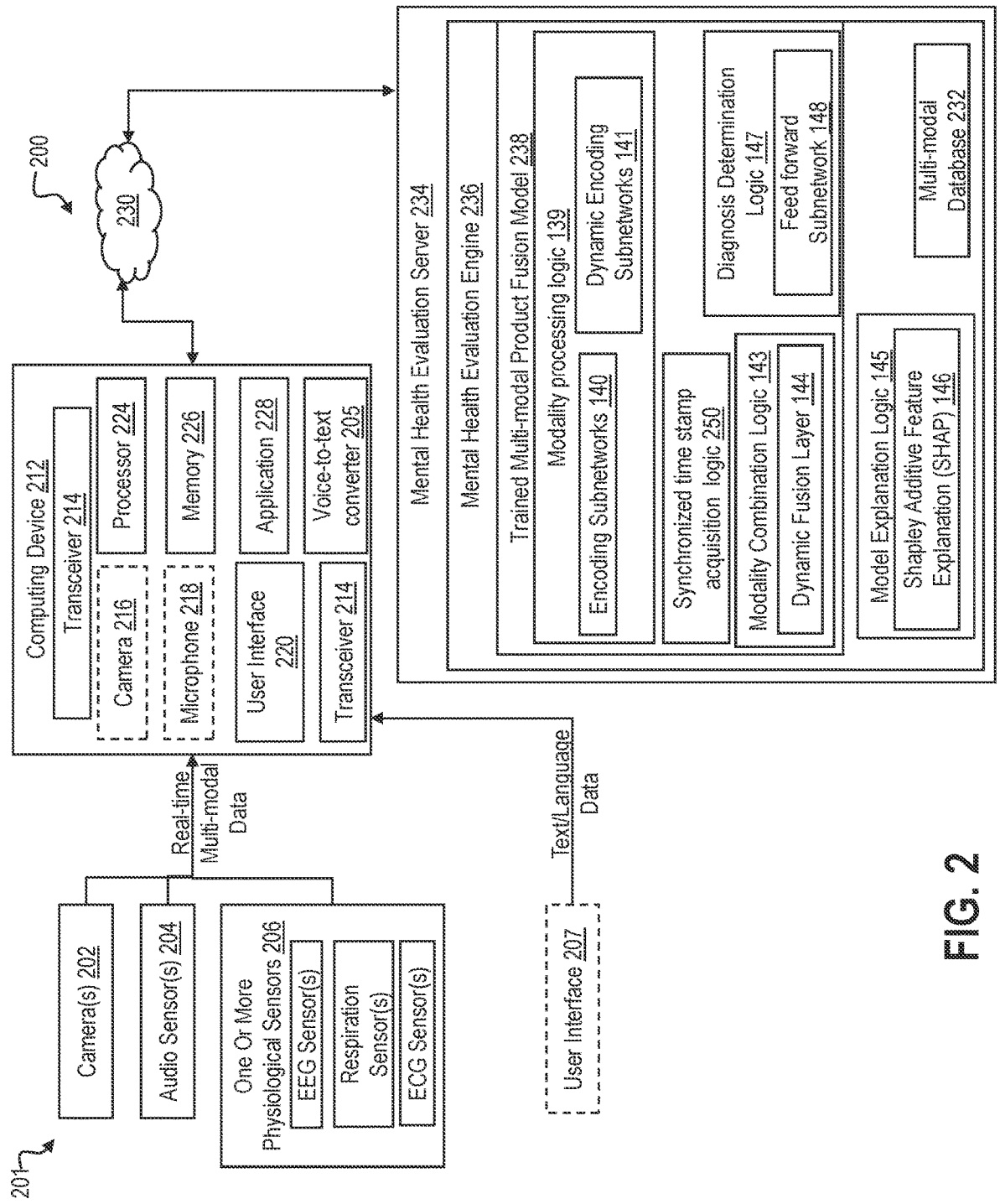
FIG. 2 is a block diagram of a mental health evaluation system including a plurality of modalities and a trained multimodal dynamic fusion model, according to an embodiment of the disclosure.

Next, FIG. 2 shows a mental health evaluation system 200, according to an embodiment. The mental health evaluation system 200 comprises a plurality of sensors and/or systems 201 that may be utilized to acquire physiological data from a patient for mental health evaluation. Indications of mental health from the plurality of sensors and/or systems 201 are combined via a trained multimodal dynamic fusion model 238 to provide more accurate and reliable mental health evaluation, as further discussed below.

Modalities

Following are various examples of modalities and types that may be utilized to implement the system and methods described herein. However, these modalities are only exemplary, and other modalities could be utilized to implement the systems and methods described herein.

Video and Audio Modalities

The plurality of sensors and/or systems 201 may include at least a camera system comprising one or more cameras 202 and an audio system comprising one or more audio sensors 204. The one or more cameras may include a depth camera, or a two-dimensional (2D) camera, or a combination thereof. In one example, the camera system may be utilized to acquire video data. The video data may be used to obtain one or more of movement, posture, facial expression, and/or eye tracking information of the patient.

In one implementation, movement information may include gait and posture information. Accordingly, video data may be used to assess gait, balance, and/or posture of the patient for mental health evaluation, and thus, video data may be used to extract gait, balance, and posture features. In one non-limiting example, a skeletal tracking method may be used to monitor and/or evaluate gait, balance, and/or posture of the patient. The skeletal tracking method includes isolating the patient from the background and identifying one or more skeletal joints (e.g., knees, shoulders, elbows, interphalangeal joints, etc.). Upon identifying a desired number of skeletal joints, gait, balance, and/or posture may be tracked in real-time or near real-time using the skeletal joints. For example, gait, balance, and posture features may be extracted from the video data, and in combination with other features, such as facial expression, gaze, etc., from the video data as discussed further below, may be used to generate a unimodal vector representation of the video data, which is subsequently used for generating a multimodal representation. As discussed further below, feature extraction from the video data may be performed using a feature extraction subnetwork, which may be a neural network based model (e.g., 1D ResNet, transformer, etc.) or a statistical model (e.g., principal component analysis (PCA)) or other models (e.g., spectrogram for audio data). The feature extraction subnetwork selected may be based on the type of modality (e.g., based on whether the modality is a video modality, audio modality, etc.) and/or the features extracted using the modality data.

In some embodiments, different feature extraction subnetworks may be used for obtaining various sets of features from a single data modality. The output from the different feature extraction subnetworks may be combined to obtain a unimodal representation. For example, while a first feature extraction subnetwork may be used for extracting facial expression features from the video data, a second different feature extraction subnetwork may be used for extracting gait features from the video data. Subsequently, all the features from each modality may be combined, via an encoding subnetwork for example, to obtain a unimodal representation (alternatively referred to herein as unimodal embedding).

Video data may be further used to detect facial expressions for mental health evaluation. In one example, a facial action coding system (FACS) may be employed to detect facial expression from video data acquired with the camera system. The FACS involves identifying presence of one or more action units (AUs) in each frame of a video acquired via the camera system. Each action unit corresponds to a muscle group movement and thus, qualitative parameters of facial expression may be evaluated based on detection of one or more AU in each image frame. The qualitative parameters may correspond to parameters for mental health evaluation, and may include a degree of a facial expression (mildly expressive, expressive, etc.), and a rate of occurrence of the facial expression (intermittent expressions, continuous expressions, erratic expressions etc.). The rate of occurrence of facial expressions may be evaluated utilizing a frequency of the detected AUs in a video sequence. Additionally, or alternatively, a level of appropriateness of the facial expression may be evaluated for mental health assessment. For example, a combination of disparate AUs may indicate an inappropriate expression (e.g., detection of AUs representing happiness and disgust). Further, a level of flatness, wherein no AUs are detected may be taken into account for mental health evaluation. Taken together, video data from the camera system is used to extract facial expression features represented by AUs. The facial expression features may be utilized in combination with the gait, balance, and posture features as well as gaze features for generating a multimodal representation.

Video data may also be used to evaluate gaze of the patient for mental health assessment. The evaluation of gaze may include a level of focus, a gaze direction, and a duration of gaze. In the evaluation of gaze, movement of eye and pupil behavior (e.g., dilation, constriction) may be tracked using video data. Accordingly, gaze features corresponding to eye movement and pupil behavior may be extracted from the video data and utilized to generate the unimodal vector representation along with gait, balance, posture, and facial expression features discussed above.

In one embodiment, during certain evaluation conditions, such as a remote evaluation condition, a fewer number of features may be extracted from a given modality data, while during some other conditions, such as during a clinical evaluation, a greater number of features may be extracted from the modality data, and considered for mental health evaluation. As a non-limiting example using video data, the fewer number of features may include facial expression, posture, and/or gaze, and the greater number of features may comprise gait and/or balance, in addition to facial expression, posture, and/or gaze. Accordingly, in some examples, the remote evaluation based on the fewer number of features may be used to obtain a preliminary analysis. Subsequently, a second evaluation based on a greater number of features may be performed for confirmation of a mental health condition determined during the preliminary analysis.

The audio system includes one or more audio sensors 204, such as one or more microphones. The audio system is utilized to acquire patient vocal response to one or more queries and tasks. In some examples, audio and video camera systems may be included in a single device, such as a mobile phone, a camcorder, etc. The video recording of the patient response may be used to extract audio and video data. The acquired audio data is then utilized to extract acoustic features indicative of a mental health status of the patient. The acoustic features may include, but not limited to a speech pattern characterized by one or more audio parameters such as tone, pitch, sound intensity, and duration of pause, a deviation from an expected speech pattern for an individual, a fundamental frequency F0 and variation in the fundamental frequency (e.g., jitter, shimmer, etc.), a harmonic to noise ratio measurement, and other acoustic features relevant to mental health diagnosis based on voice pathology. In one example, the acoustic features may be represented by Mel Frequency Cepstral Coefficents (MFCCs) obtained via a cepstral processing of the audio data.

Physiological Sensor Modalities

While audio and video modalities may be used to characterize behavioral phenotypes, mental health conditions exhibit changes in physiological phenotypes (e.g., ECG activity, respiration, etc.), structural phenotypes (e.g., abnormal brain structure) and associated functional phenotypes (e.g., brain functional activity), which may be utilized to obtain a comprehensive and more accurate evaluation of mental health. Therefore, data from physiological sensors, and functional medical imaging devices, may be included in generating a multimodal representation that is subsequently used to classify mental health condition. Accordingly, the plurality of sensors and/or systems may include one or more physiological sensors 206. The one or more physiological sensors 206 may include Electroencephalography (EEG) sensors, Electromyography (EMG) sensors, Electrocardiogram (ECG) sensors, or respiration sensors, or any combination thereof. Physiological sensor data from each of the one or more physiological sensors may be used to obtain corresponding physiological features representative of mental health. That is, unimodal sensor data representation from each physiological sensor may be obtained according to physiological sensor data from each physiological sensor. Each unimodal sensor representation may be subsequently used to generate a multimodal representation for mental health evaluation.

Medical Imaging Modalities

The plurality of modalities 201 may further include one or more medical imaging devices 208. In some examples, medical image data may be acquired along with behavioral (audio, video, language) and/or other physiological data in a clinical setting. The dynamic fusion model in such an example may receive medical image data, physiological data and/or behavioral data, and output a mental health classification. Medical image data from one or more medical imaging devices may be utilized to obtain brain structure and functional information for mental health diagnosis. For example, imaging biomarkers corresponding to different mental health conditions may be extracted using medical image data. Example medical imaging devices include magnetic resonance imaging (MRI) and related modalities such as, functional magnetic resonance imaging (fMRI), T1-weighted MRI, diffusion weighted MRI, etc., positron emission tomography (PET), and computed tomography (CT). It will be appreciated that other medical imaging modalities, in particular, neuroimaging modalities, that provide brain structural and/or functional biomarkers for clinical evaluation of mental health may be used, and is within the scope of the disclosure. Medical image data acquired via one or more medical imaging devices may be used to extract brain structural and functional features (e.g., clinical biomarkers of mental health disease, normal health features, etc.) to generate corresponding unimodal representations. In one example, a plurality of unimodal representations of each medical imaging data modality may be generated, which may be fused to obtain a combined medical image data modality representation. The combined medical image modality representation may be subsequently used to generate multimodal representation by combining with one or more other modalities (e.g., audio, video, physiological sensors, etc.). In another example, each medical image modality representation (that is, unimodal representation from each medical imaging modality) may be combined with the one or more other modalities without generating the combined medical image modality representation.

Computing Device(s) for Preprocessing and Implementation of the Dynamic Fusion Model Mental health evaluation system 200 includes a computing device 212 for receiving a plurality of data modalities acquired via the plurality of sensors and/or systems 201. The computing device 212 may be any suitable computing device, including a computer, laptop, mobile phone, etc. The computing device 212 includes one or more processors 224, one or more memories 226, and a user interface 220 for receiving user input and/or displaying information to a user.

In one implementation, the computing device 212 may be configured as a mobile device and may include an application 228, which represent machine executable instructions in the form of software, firmware, or a combination thereof. The components identified in the application 228 may be part of an operating system of the mobile device or may be an application developed to run using the operating system. In one example, application 228 may be a mobile application. The application 228 may also include web applications, which may mirror the mobile application, e.g., providing the same or similar content as the mobile application. In some implementations, the application 228 may be used to initiate multimodal data acquisition for mental health evaluation. Further, in some examples, the application 228 may be configured to monitor a quality of data acquired from each modality, and provide indications to a user regarding the quality of data. For example, if audio data quality acquired by a microphone is less than a threshold value (e.g., sound intensity is below a threshold), the application 228 may provide indications to the user to adjust a position of the microphone.

The application 228 may be used for remote mental health evaluation as well as in-clinic mental health evaluation. In one example, the application 228 may include a clinician interface that allows an authenticated clinician to select a desired number of modalities and/or specify modalities from which data may be collected for mental health evaluation. The application 228 may allow the clinician to selectively store multimodal data, initiate mental health evaluation, and/or view and store results of the mental health evaluation. In some implementations, the application 228 may include a patient interface and may assist a patient in acquiring modality data for mental health evaluation. As a non-limiting example, the patient interface may include options for activating a camera 216 and/or microphone 218 that are communicatively coupled to the computing device and/or integrated within the computing device. The camera 216 and microphone 218 may be used to acquire video and audio data respectively for mental health evaluation.

In one example, memory 226 may include instructions that when executed causes the processor 224 to receive the plurality of data modalities via a transceiver 214 and further, pre-process the plurality of modality data. Pre-processing the plurality of data modalities may include filtering each of plurality of data modalities to remove noise. Depending on the type of modality, different noise reduction techniques may be implemented. In some examples, the plurality of data modalities may be transmitted to mental health evaluation server 234 from the computing device via a communication network 230, and the pre-processing step to remove noise may be performed at server 234. For example, the server 234 may be configured to receive the plurality of data modalities from the computing device 212 via the network 230 and pre-process the plurality of data modalities to reduce noise. The network 230 may be wired, wireless, or various combinations of wired and wireless.

The server 234 may include a mental health evaluation engine 236 for performing mental health condition analysis. In one example, the mental health evaluation engine 236 includes a trained machine learning model, such as a multimodal fusion model 238, for performing mental health evaluation using the plurality of noise-reduced (or denoised) data modalities. The multimodal dynamic fusion model 238 may include several sub-networks and layers for performing mental health evaluation. Example network architectures of the multimodal dynamic fusion model 238 are described with respect to FIG. 5A.

The server 234 may include a multimodal database 232 for storing the plurality of modality data for each patient. The multimodal database may also store plurality of training and/or validation datasets for training and/or validating the multimodal fusion model for performing mental health evaluation. Further, the mental health evaluation output from the multimodal fusion model 238 may be stored at the multimodal database 232. Additionally, or alternatively, the mental health evaluation output may be transmitted from the server to the computing device, and displayed and/or stored at the computing device 212.

Figure 3A:
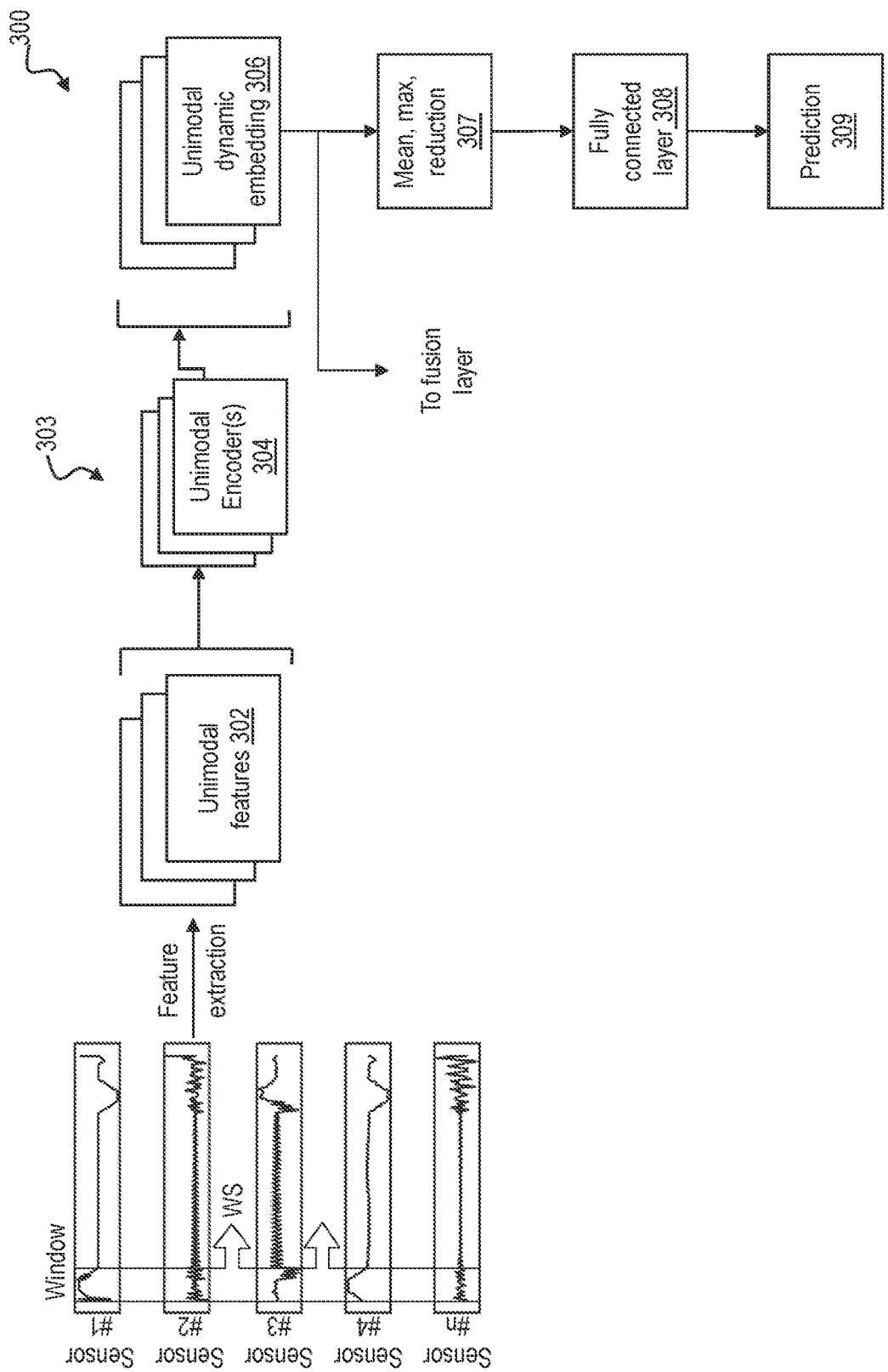
FIG. 3A is a schematic of an architecture of a unimodal architecture comprising a unimodal dynamic encoder for generating unimodal dynamic embeddings, according to an embodiment of the disclosure.

Multimodal Dynamic Fusion Model Architecture
Unimodal Encoders and Unimodal Dynamic Embeddings FIG. 3A shows a high-level block diagram of a network architecture of a unimodal classification network 300 for generating unimodal dynamic embeddings which is then used for fusion by the multimodal dynamic fusion model. The unimodal network 300 may be implemented by server 234, computing device 212, or a combination thereof. The multimodal dynamic fusion model has a modular architecture including at least a dynamic encoder module 303, a fusion layer, and a mental health inference module. In some examples, the multimodal dynamic fusion model may implement a model explanation generator, such as a SHAP, for indicating one or more important features based on which the multimodal fusion model generated the classification outcome as further discussed below. The encoder module 303 may be an example of the dynamic encoder subnetwork of the modality processing logic 143, discussed at FIG. 1B. The encoder module comprises one or more dynamic encoder subnetworks 1, 2, etc., and up to N. Each of the one or more dynamic encoder subnetworks receives, as input, unimodal features extracted from modality data from at least one of a plurality of sensors and/or systems, such as the plurality of sensors and/or system 201. As shown at FIG. 3A, a plurality of unimodal feature sets 302 extracted from a plurality of modality datasets (acquired from a plurality of sensors) are input into corresponding dynamic unimodal encoders to generate a plurality of unimodal dynamic feature sets. For example, a first feature set extracted from modality data (acquired via a first sensor) is input to the first encoder subnetwork, a second feature set extracted from modality data (acquired via a second sensor) is input to the second encoder subnetwork, and so on up to Nth feature set extracted from Nth modality data (acquired from a Nth sensor) is input to the Nth encoder subnetwork.

Accordingly, the unimodal network 300 generates unimodal dynamic embeddings 306 for each data modality via a corresponding unimodal dynamic encoder 304.

Figure 3B:
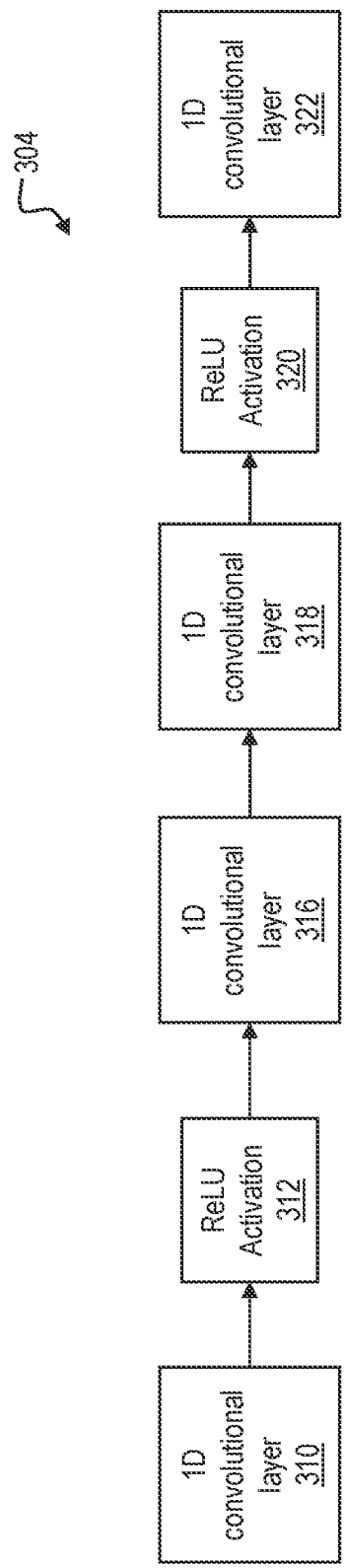
FIG. 3B is a schematic of the unimodal dynamic encoder of FIG. 3A.

The unimodal encoder 304 is shown in FIG. 3B and comprises stacked convolution blocks. Each convolution block includes a 1D convolution layer (that performs strided 1D convolution) followed by batch normalization and ReLU activation function. While the present example shows four 1D convolutional layers, a number of 1D convolutional layers may be greater or less than four. For example, the number of 1D convolutional layers based on the data modality and/or optimization during pre-training. For pre-training, the output of the block 306 is flattened through max and mean pooling. These two vectors are concatenated and input to a fully-connected layer 308 followed by sigmoid activation. After pre-training, the pooling and the fully connected layers 306 and 306 are discarded and an output dynamic embedding (block 306) is passed on to a fusion layer of the multimodal fusion model. By utilizing 1D convolutional layers, patterns from the time series features are extracted and represented as dynamic unimodal embeddings.

As used herein, "static embedding" is a vector of numeric value, having a particular dimensionality, and "dynamic embedding" is a vector of numeric value and comprising timing information, having a particular dimensionality.

Pre-Processing

In one example, one or more of the first modality data, the second modality data, and up to Nth modality data may be pre-processed before being input to the respective encoder subnetwork. Each modality data may be pre-processed according to the type of data acquired from the modality. For example, audio data acquired from an audio modality (e.g., microphone) may be processed to remove background audio and obtain a dry audio signal of a patient's voice. Video data of the patient acquired from a camera may be preprocessed to obtain a plurality of frames and further, the frames may be processed to focus on the patient or a portion of the patient (e.g., face). Further, when language or text data is preprocessed, noise may be special characters that do not impart useful meaning and thus, noise removal may include removing characters or texts that may interfere with the analysis of text data. Sensor data may be preprocessed by band pass filtering to include sensor data within an upper and lower threshold.

In general, the pre-processing of one or more of the first, second, and up to Nth modality data may include one or more of applying one or more modality specific filters to reduce background noise, selecting modality data that has a quality level above a threshold, normalization, and identifying and excluding outlier data, among other modality specific pre-processing. The pre-processing of each modality data may be performed by a computing device, such as computing device 212, before its transmitted to the server for mental health analysis. As a result, less communication bandwidth may be required, which improves an overall processing speed of mental health evaluation. In some examples, the pre-processing may be performed at the server implementing the dynamic fusion model, prior to passing the plurality of modality data through the dynamic fusion model.

In one embodiment, pre-processing the modality data may include extracting corresponding modality features related to mental health evaluation from the modality data. For example, a rich representation of audio features corresponding to mental health conditions may be generated using audio data from an audio modality (e.g., microphone); a rich representation of video features corresponding to mental health condition may be generated using video data from a video modality (e.g., camera); a rich representation of EEG features corresponding to mental health condition may be generated from EEG data from a EEG sensor; a rich representation of text features associated with mental condition may be generated using text data corresponding to spoken language (or based on user input entered via a user input device); and so on. Feature extraction may be performed using a trained neural network model or any feature extraction method depending on the modality data and/or features extracted from the modality data, where the extracted features include markers for mental health evaluation.

Figure 4A:
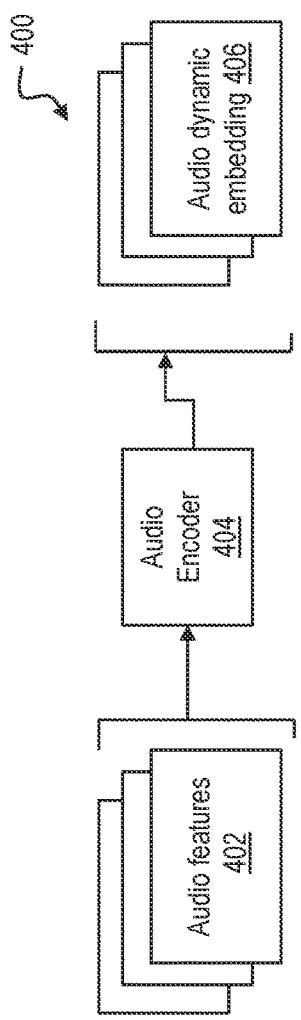
FIGS. 4A, 4B, and 4C shows a schematic depicting generation of example unimodal dynamic embeddings via respective unimodal dynamic encoders, according to an embodiment of the disclosure.
Figure 4B:
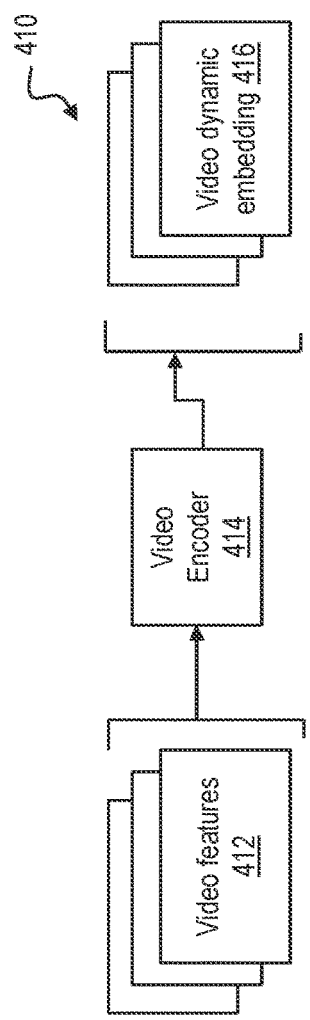
Figure 4C:
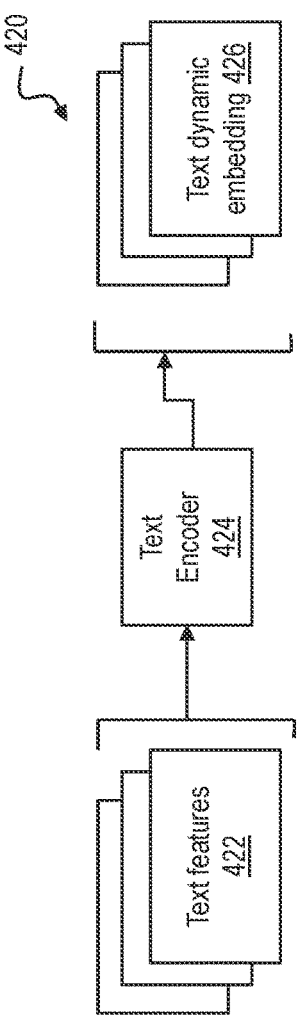

FIGS. 4A, 4B, and 4C show example generation of audio, video, and text (alternatively referred to as language) dynamic embeddings using audio, video, and text data. For example, a trimodal mental health evaluation may be performed using audio, video, and text data collected via a camera, microphone, and speech to text conversion. Audio features 402, video features 412, and text features 422 may be extracted from audio, video, and text data at a desired time resolution (e.g., 0.1 sec). Further, audio dynamic embeddings 406, video dynamic embeddings 416, and text dynamic embeddings 426 may be generated using an audio dynamic encoder 404, a video dynamic encoder 414, and a text dynamic encoder 424 respectively. The architecture of the audio, video, and text encoders may be similar to the encoder described above at FIG. 3B. Each of the audio, video, and text encoders are pre-trained as discussed above.

FIG. 5 shows an example network architecture of a multimodal dynamic fusion model 500, according to one or more embodiments of the disclosure. The multimodal dynamic fusion model 500 is an example of multimodal fusion models 138 and 238 at FIGS. 1B and 2 respectively.

The multimodal fusion model 500 comprises unimodal encoders 404, 414, 424 for generating unimodal dynamic embeddings. As discussed above, unimodal encoders include stacked convolution blocks (1D convolution layer followed by batch normalization and ReLU activation) for extracting dynamic embeddings from each of the individual modalities. The dynamic embeddings are concatenated (502) and passed on to a Transformer Encoder, which performs dynamic attention fusion (512) to learn a multimodal representation for classification. By using convolutional encoders to generate dynamic embeddings and using transformer encoders to fuse the dynamic embeddings and efficiently process the sequence, information across modalities is integrated within a temporal context (e.g. facial expression change and vocal inflection while a salient word is uttered).

Figure 5B:
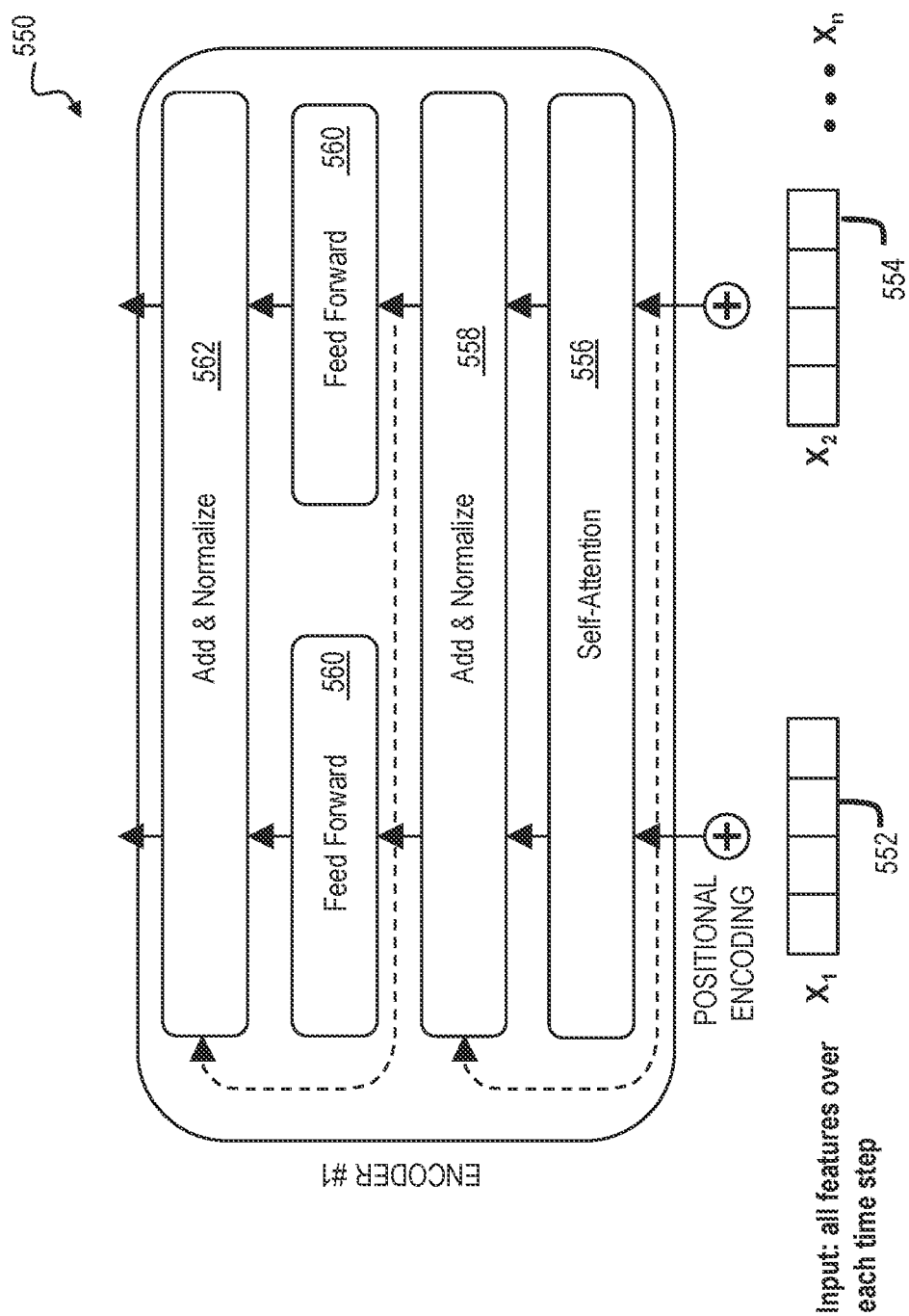
FIG. 5B is a schematic of an example transformer encoder used for fusion, according to an embodiment of the disclosure.

An example Transformer Encoder 550 is shown at FIG. 5B. The transformer encoder 550 comprises stacked transformer encoder blocks. Each transformer encoder block includes a Multi-Head Self Attention layer 556, an add & normalize layer 558, a feedforward network 560, and an add & normalize layer 562. In particular, the transformer encoder comprises of multi-head self-attention blocks. The self-attention mechanism encodes the context for each temporal step. This is done through learning a key, query and value for each step and the context is learnt through passing the query and key to a mathematical function (usually matrix multiplication followed by SoftMax). Rather than only computing the attention once, the multi-head mechanism runs through the attention multiple times in parallel. The independent attention outputs are concatenated and linearly transformed into the expected dimensions. This enables us to learn multiple dependencies or contexts that might not be captured by a single attention mechanism. The number of heads is determined by hyperparameter tuning.

In one example, after feature extraction, a first number of time steps (e.g., 153) may be present at a resolution of 0.1 seconds each. After the unimodal encoder using 1D convolution, the time dimension is reduced to a second number of time steps (e.g., 39) less than the first number of time steps because of the convolution operation over time which includes weighted summing over a time window (also called kernel). X1, X2 . . . Xn in FIG. 5B are the concatenated unimodal embeddings over "n" consecutive "time" points. Continuing with the example above, 39 consecutive time points X1, X2, . . . X39 are input into the encoder. Further positional encoding (e.g., sine-cosine based encoding) is applied to the inputs of all features over each time step such as inputs 552 and 554 to maintain the timing information.

The output of the Transformer Encoder is a high dimensional multimodal dynamic representation, which is then flattened through max and mean pooling (516) to generate multimodal static embedding. These two vectors are then concatenated and passed on to a fully-connected layer 520 for mental health classification. SHAP values may be then generated (524) for each prediction.

In the present example, inputs from audio, video, and text modalities are used. It will be appreciated that the multimodal dynamic fusion model 500 may generate mental health evaluation output from data inputs from more additional sensors. In one example, plurality of time-series datasets from a plurality of sensors (e.g., audio sensor, video sensor, text generator, EEG, ECG, etc.) may be acquired (e.g., EEG and/or ECG may be acquired while a patient is recorded via a video camera when responding to questions and/or performing vocal exercises via a mental health application). The plurality of time-series datasets may be processed, via a modality processing logic discussed above to extract a set of features from each of the plurality of time-series datasets. Further, the set of features includes time stamp information or timing information that will be synchronized across modalities/sensors. The set of features are then processed via a corresponding dynamic encoder, such as encoder shown at FIG. 3B to generate unimodal dynamic embeddings having timing information.

SHAP Based Feature Importance

One of the key issues in machine learning systems for health-care is lack of interpretability, particularly in understanding feature importance. This is particularly the case for deep models like those we use in this study, which are useful in extracting information from rich modalities like audio, video, and text, but are difficult to interpret due to their large numbers of model weights. Improvements in interpretability could provide important validation by clinicians, and may provide a pathway for digital marker discovery. Herein, SHapley Additive exPlanations (SHAP), an additive feature attribution method is used to explain the output of the machine learning model (not to be confused with the SHAPS questionnaire for assessing anhedonia). Via SHAP, feature importance for each input variable may be computed using SHAP values for all the input features (which are time series features) over each point of time.

Model Training and Evaluation

The unimodal encoders are pre-trained. For the unimodal encoder pre-training, the following hyperparameters that may be tuned include: the number of CNN layers, the number of hidden nodes in each layer, the kernel size, the number and size of fully connected layers. Dropout may be applied to all non-linear layers with a 0.2 probability of being zeroed. The Adam optimizer with L2 weight decay and binary cross-entropy loss may be used. After pre-training, the pooling and the fully connected layers are discarded and an output dynamic embedding for each modality is passed on to the fusion layer.

The dynamic embeddings from these were fused using the Transformer Encoder and used for model training. In one example, a 60-20-20 random train-validation-test split may be used. For each of the three binary classification problems, random search may be used to perform hyperparameter tuning using the validation set. For the multimodal training, the hyperparameters that may be tuned include the number of transformer encoder layers, the number of hidden nodes and the number of multihead attention heads in the transformer layers, the number and size of fully connected layers. Dropout may be applied to the fully connected layers with a 0.4 probability of being zeroed. The Adam optimizer with L2 weight decay and binary cross-entropy loss may be used. A binary cross-entropy loss may be used. The entire model may be implemented in PyTorch.

A SHAP Gradient Explainer algorithm which is an extension of the Integrated Gradients algorithm may be employed for determining important features. Under the assumptions of additive feature attribution, the SHAP value for a given input variable can be approximated as the expectation of gradients that were computed for randomly generated input samples after adding Gaussian noise to each input for different base-lines/references. In this way, SHAP scores for each of input variables for each subject and time point may be calculated. These values may then be summarized over the subjects and temporal axes, resulting in a global importance value for each feature.

Turning to FIG. 6 it shows a flow chart illustrating a high-level method 600 for evaluating a mental health condition of a patient based on multimodal data from a plurality of modalities. The method 600 may be executed by a processor, such as processor 224 or one or more processors of mental health evaluation server 234 or a combination thereof. The processor executing the method 500 includes a trained multimodal dynamic fusion model, such as model 500 at FIG. 5A. As discussed above, the trained multimodal dynamic fusion model is trained to classify one or more mental health conditions, including but not limited to depression, anxious depression, and anhedonic conditions, or output a regression result pertaining to the one or more health conditions.

In one example, the method 600 may be initiated responsive to a user (e.g., a clinician, a patient, a caregiver, etc.) initiating mental health analysis. For example, the user may initiate mental health analysis via an application, such as app 228. In another example, the user may initiate mental health data acquisition; however, the data may be stored and the evaluation of mental health condition may be performed at a later time. For example, mental health analysis may be initiated when data from a desired number and/or desired types of modalities (e.g., audio, video, text, and imaging) are available for analysis.

At 602, the method 600 includes receiving a plurality of datasets from a plurality of sensors and/or systems and/or devices. The plurality of sensors and/or systems include two or more of the sensors and/or systems and/or devices 201 described at FIG. 2. For example, the plurality of sensors and/or systems and/or devices may include two or more of audio, video, text, and physiological sensor, camera system 202, audio sensors 204, user interface 207, voice to text converter 205, and one or more physiological sensors 206. As a non-limiting example, in a trimodal system, a patient response may be evaluated using a video recording, and patient input via the user interface. As such, video data, and audio data from the recording, and text data according to text converted from spoken language via the speech to text converter and/or patient text input via the user interface may be transmitted to the processer implementing the trained multimodal dynamic fusion model. In some examples, modality data may be processed in real time using the dynamic fusion model, and as such, real-time or near real-time mental health evaluation by implementing the dynamic fusion model is also within the scope of the disclosure. Further, timing information may be acquired for each of the plurality of datasets.

Next, in one example, at 603, the method 600 includes synchronizing timing across the plurality of data modalities. For example, time stamps may be aligned and timing differences (e.g., due to jitter, dropped packets, etc.) may be accounted for. In this way, timing information across the plurality of data modalities is preserved. For example, for each time duration (e.g. 0.1 sec), corresponding audio, video, and text features are correlated and the feature information as well as the timing information is captured. It will be appreciated that other time synchronization approaches may be applied and are within the scope of the disclosure.

In some examples, a time lag between two or more modalities may be accounted for. For example, if there a lag between audio and video data acquisitions, the time differences may be determined and accounted during the synchronization. Accordingly, in one example, a short test acquisition may be performed to determine a base line for timing for synchronization purposes.

Next, at 604, the method 600 includes pre-processing each of the plurality of datasets to extract mental health features from each dataset at a desired timing resolution. For example, audio, video, and text features may be extracted at a timing resolution of 0.1 seconds. In one example, pre-processing each of the plurality of datasets includes reducing and/or removing noise from each raw dataset. For example, a signal processing method, such as band-pass filtering may be used to reduce or remove noise from a dataset. Further, the type of signal processing used may be based on the type of dataset. Pre-processing each dataset further includes passing the noise-reduced/denoised dataset or the raw dataset through a trained subnetwork, such as a trained neural network, for extracting a plurality of mental health features from each dataset. Any other feature extraction method that is not based on neural networks may be also used. In some examples, pre-processing may be performed to improve input signal quality by implementing one or more flags. The one or more flags include but not limited to Video frame capture failures (poor lighting conditions), Missing transcriptions (excessive background noise or multiple persons speaking), Illegible speech, and Inconsistent responses between similar questions of clinical scales. In some examples, a segment within a time window from each of the plurality of datasets is extracted. Further, the segment from each of the plurality of datasets may be time synchronized before pre-processing to extract features.

For a trimodal example including audio, video, and text, a plurality of frames of the video data may be passed through a trained neural network model comprising a trained convoluted neural network for segmenting, identifying and extracting a plurality of action units according to FACS. Further, audio data may be processed to generate a cepstral representation of the audio data and a plurality of MFCC may be derived from the cepstral representation, and text data may be processed according to pre-trained or fine-tuned BERT model to obtain one or more sequences of vectors. In some examples, one or more datasets may be preprocessed using statistical methods, such as principal component analysis (PCA), for feature extraction. As a non-limiting example, EEG data may be preprocessed to extract a plurality of EEG features pertaining to mental health evaluation.

Next, at 604, the method 600 includes generating unimodal dynamic embeddings via unimodal dynamic encoders, which are 1D convolutional encoders for capturing timing information across all features from all input modalities. For example, upon extracting mental health features from each dataset, the features from each dataset may be passed through a corresponding trained dynamic encoding subnetwork (e.g., FIG. 3B) to generate unimodal dynamic embeddings for each dataset. For example, a set of mental features extracted from a dataset may be input into a trained dynamic encoding neural network to generate unimodal dynamic embeddings, which are vector representations of the input features including timing information for a given modality. In this way, unimodal dynamic embeddings for each modality used for mental health evaluation may be generated.

Next, at 606, a high-dimensional multimodal representation is generated by fusing the unimodal dynamic embeddings. In one example, a transformer encoder with positional encoding is used for fusing unimodal embeddings. The unimodal embeddings are first concatenated and passed on to a Transformer Encoder, comprising of a plurality of stacked transformer encoder blocks. The transformer applies a self-attention mechanism that directly models relationships between input vectors. The transformer allows for significantly more parallelization. The transformer encodes each position and applies the attention mechanism to relate input features at each time-step, which may be parallelized for all time-steps.

Upon obtaining the high dimensional representation, the method 600 proceeds to 614 to generate a low dimensional representation. In one example, a cross-attention mechanism may be utilized to generate the low dimensional representation. In other examples, any other dimensionality reduction method may be implemented. In particular, since the interactions between the different modalities are captured in the high dimensional representation, any dimensionality reduction mechanism may be used and the interacting features for mental health determination would still be preserved. The dimensionality reduction mechanisms may include a feed-forward neural network, a convolutional neural network, a long short-term memory network (LSTM), or a transformer. Upon obtaining the low dimensional representation, the method 600 proceeds to 616.

In another embodiment, the method 600 may proceed from step 606 to 616 to generate one or more of mental health evaluation outputs. In particular, at 616, generating the one or more mental health evaluation outputs includes inputting the high dimensional representation (or the low dimensional representation if step 614 is performed) into a trained mental health inference module. The trained mental health reference module may include one or more feed forward networks. For example, a first feed forward network trained by a supervised classification method may be used to output a binary classification result (e.g., depressed or not depressed). A second feed forward network may be trained by a supervised classification method to output a multi-class classification result (e.g., different levels of depression). A third feed forward network may be trained by a supervised regression method to output a regression result, which may be further used for multiclass or binary classification.

Example Trimodal Mental Health Evaluation

Example mental health evaluation using a multimodal fusion model to identify symptoms of mood disorders using audio, video and text collected using a smartphone app is described below. The mood disorder symptoms include depression, anxiety, and anhedonia, which may be predicted using a trained multimodal fusion model.

Data

Example dataset was generated using questionnaires for multiple mood disorder symptoms including depression, anxiety, and anhedonia, which was predicted using multimodal modeling. The data used was collected remotely through an interactive smartphone application that was available to the U.S. general population through Google Play and Apple App Store under IRB approval. (1) Demographic Variables and Health History (2) Self-reported clinical scales including Patient Health Questionnaire-9 (PHQ-9), Generalized Anxiety Disorder-7 (GAD-7), and Snaith Hamilton Pleasure Scale (SHAPS) and (3) Video recorded vocal expression activities (where participants were asked to record videos of their faces while responding to prompts) were collected on each of 3002 unique participants. The entire set of video tasks took less than five minutes, and participants could provide data up to three times (across 4 weeks), for a total of 3 sessions (not all participants completed 3 sessions).

Audio Features

These represent the acoustic information in the response. Each audio file was denoised, and unvoiced segments were removed. For each audio file, a total of 123 audio features were extracted from the voice segments at a resolution of 0.1 s including prosodic (Pause rate, speaking rate etc.), glottal (Normalised Amplitude Quotient, Quasi-Open-Quotient etc.), spectral (Mel-frequency cepstral coefficients, Spectral Centroid, Spectral flux, Mel-frequency cepstral coefficients spectrograms etc.) and chroma (Chroma Spectogram) features.

Video Features

These represent the facial expression information in the response. For each video, 3D facial landmarks were computed at a resolution of 0.1 seconds. From these, 22 Facial Action Units were computed for modeling. For each video file, 22 Facial Action Unit features were derived from 3D facial landmarks which were computed at a resolution of 0.1 s. 3D facial landmarks are much more robust to noise than 2D facial landmarks. As such, 3D facial landmarks are extracted. In particular, for remote data collection, 3D facial landmarks were used due to more robustness compared to 2D facial landmarks.

Text Features

These represent the linguistic information in the response. Each audio file was transcribed using Google Speech-to-Text and 52 text features were computed including affective features, word polarity and word embeddings. For each file, 52 text features were extracted including affect based features viz. arousal, valence and dominance rating for each word using Warriner Affective Ratings, polarity for each word using TextBlob, contextual features such as word embeddings using doc2vec etc.

Quality Control

In contrast to prior approaches, where the data was collected under clinical supervision (e.g. the DAIC dataset, the data utilized herein was collected remotely on consumer smartphones. Consequently, this data includes more noise that needed to be addressed before modeling. There were two broad sources of noise: (1) Noisy medium (e.g. background audio noise, video failures and illegible speech) (2) Insincere participants (e.g. participant answering "blah" to all prompts). Using the metadata, scales and extracted features, quality control flags were designed to screen participants. Out of 6020 collected sessions, 1999 passed this stage. The developed flags can be pre-built into the app for data collection.

Multimodal Machine Learning Approach

A multimodal machine learning approach to classify symptoms of mood disorders. Specifically, the audio, video and textual modalities for the 1999 sessions were used as input, and three classifications were performed to predict binary outcome labels related to the presence of symptoms of (1) depression (total PHQ-9 score >9), (2) anxiety (total GAD-7 score >9), and (3) anhedonia (total SHAPS score >25)). Here, 71.4% of participants had symptoms of depression, 57.8% of participants had symptoms of anxiety and 67.3% of participants had symptoms of anhedonia. This dataset was much larger than the commonly used DAIC dataset in AVEC 2019 (N=275) and also contained a higher percentage of individuals with depression symptoms (our dataset=72%, AVEC=25%).

Model

Model Architecture

Figure 5C:
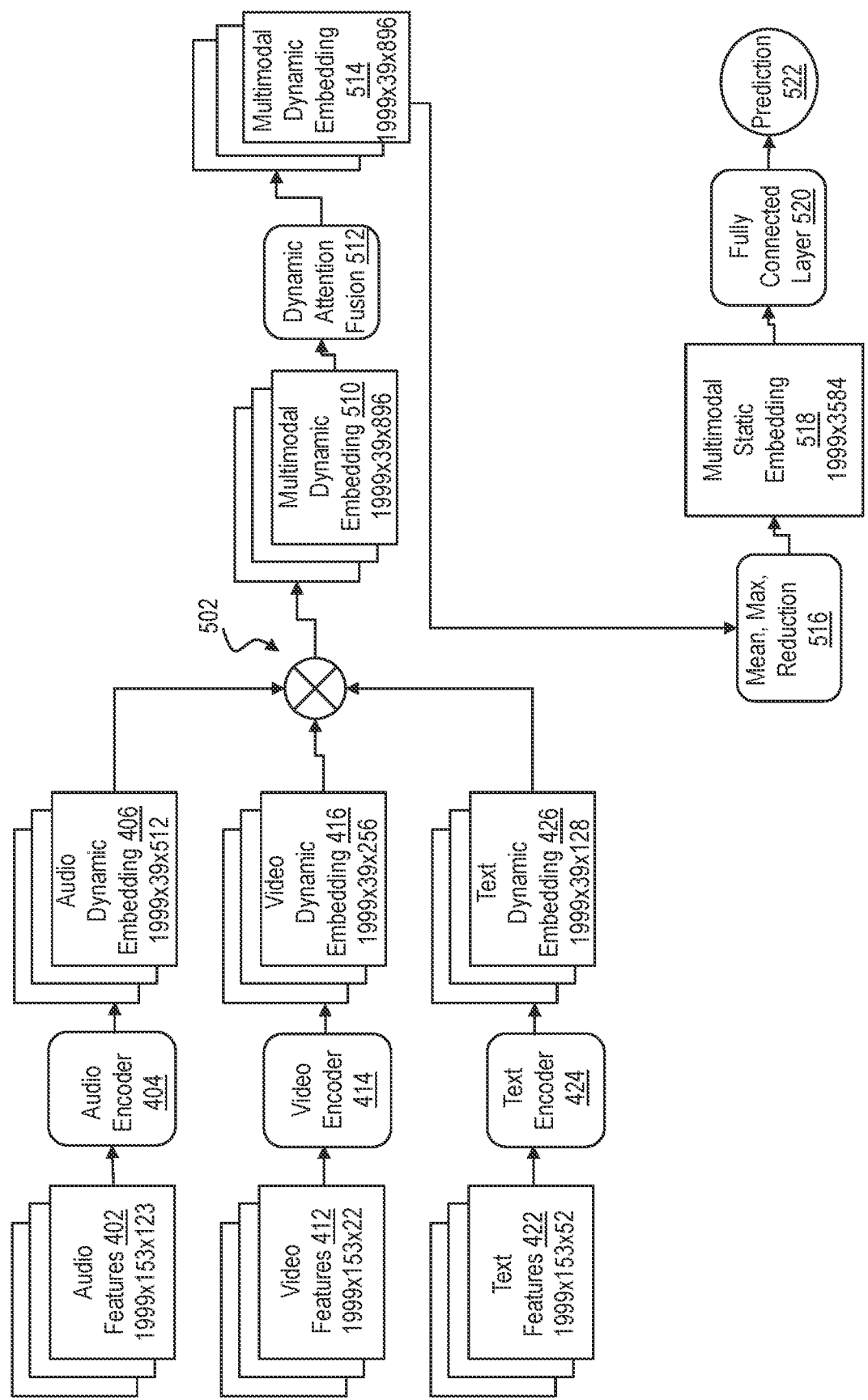
FIG. 5C is another schematic of a trained multimodal dynamic fusion model implemented for mental health evaluation using audio, video, and text modalities, according to an embodiment of the disclosure.

A multimodal classification framework is provided. The multimodal classification framework comprises unimodal encoders of stacked convolution blocks (1D convolution layer followed by batch normalization and ReLU activation) extracted dynamic embeddings from each of the individual modalities. These were concatenated and passed on to a Transformer Encoder to learn a multimodal representation for classification. The multimodal architecture is in contrast to existing literature which used LSTM-based uni-modal embeddings instead of convolution, which are then collapsed across the time dimension prior to fusion, as opposed to our dynamic fusion. In the architecture, time dimension is not collapsed prior to fusion. This allowed to integrate information across modalities within a temporal context (e.g. facial expression change and vocal inflection while a salient word is uttered) through dynamic embeddings to form a multimodal sequence and efficiently process this sequence using a trans-former. The complete architecture is shown in FIGS. 5A and 5C. FIG. 5C shows the architecture in FIG. 5A, and further includes dimensions.

Model Training and Evaluation

The unimodal encoders were pre-trained; the dynamic embeddings from these were fused using the Transformer Encoder and used for model training. A 60-20-20 random train-validation-test split was used and the F1 score was computed for each split. This iteration was repeated 100 times and the median test F1 score was reported as the evaluation metric.

For each of the three binary classification problems, random search was used to do hyperparameter tuning using the validation set. For the unimodal encoder pre-training, the following hyperparameters were tuned: the number of CNN layers, the number of hidden nodes in each layer, the kernel size, the number and size of fully connected layers. Dropout was applied to all non-linear layers with a 0.2 probability of being zeroed. The Adam optimizer with L2 weight de-cay and binary cross-entropy loss was used. The model was trained for 30 epochs. After pre-training, the pooling and the fully connected layers was discarded and an output dynamic embedding was passed on to the fusion layer. For the multimodal training, the following hyperparameters were tuned: the number of transformer encoder layers, the number of hidden nodes and the number of multihead attention heads in the transformer layers, the number and size of fully connected layers. Dropout was applied to the fully connected layers with a 0.4 probability of being zeroed. The Adam optimizer with L2 weight decay and binary cross-entropy loss was used. A binary cross-entropy loss was used. The model was trained for 30 epochs. The entire model was implemented in PyTorch.

SHAP Based Feature Importance

One of the key issues in machine learning systems for health-care is lack of interpretability, particularly in understanding feature importance. This is particularly the case for deep models like those we use in this study, which are useful in extracting information from rich modalities like audio, video, and text, but are difficult to interpret due to their large numbers of model weights. Improvements in interpretability could provide important validation by clinicians, and may provide a pathway for digital marker discovery. SHapley Additive exPlanations (SHAP) (Lundberg & Lee, 2017), an additive feature attribution method was used to explain the output of any machine learning model (not to be confused with the SHAPS questionnaire for assessing anhedonia). This enabled to compute feature importance for each input variable using SHAP values.

A SHAP Gradient Explainer algorithm which is an extension of the Integrated Gradients algorithm was employed. Under the assumptions of additive feature attribution, the SHAP value for a given input variable can be approximated as the expectation of gradients that were computed for randomly generated input samples after adding Gaussian noise to each input for different base-lines/references. This allowed calculation of SHAP scores for each input variables for each subject and time point. These values were summarized over the subjects and temporal axes, resulting in a global importance value for each feature.

Experiments and Results

Multimodal Classification of Symptom Severity

The CNN-Dynamic Attention Fusion multimodal method outperformed state of the art works employing static unimodal embeddings: (A) LSTM-Concatenation (Al Hanai et al., 2018) (B) BiLSTM-Static Attention (Ray et al. Multi-level attention network using text, audio and video for depression prediction. In Proceedings of the 9th International on Audio/Visual Emotion Challenge and Workshop, AVEC '19, pp. 81-88, New York, NY, USA, 2019. Association for Computing Machinery. (Hereinafter, Ray et al., 2019) (C) LSTM-Tensor Fusion (Qureshi, S. A., et al. The verbal and non-verbal signals of depression combining acoustics, text and visuals for estimating depression level. 2019. (Hereinafter, Qureshi et al., 2019)) in multimodal classification of symptoms across three domains: depression (PHQ-9 scale), anxiety (using GAD-7 scale) and anhedonia (using SHAPS scale). Two different aspects of performance were compared.

Figure 7:
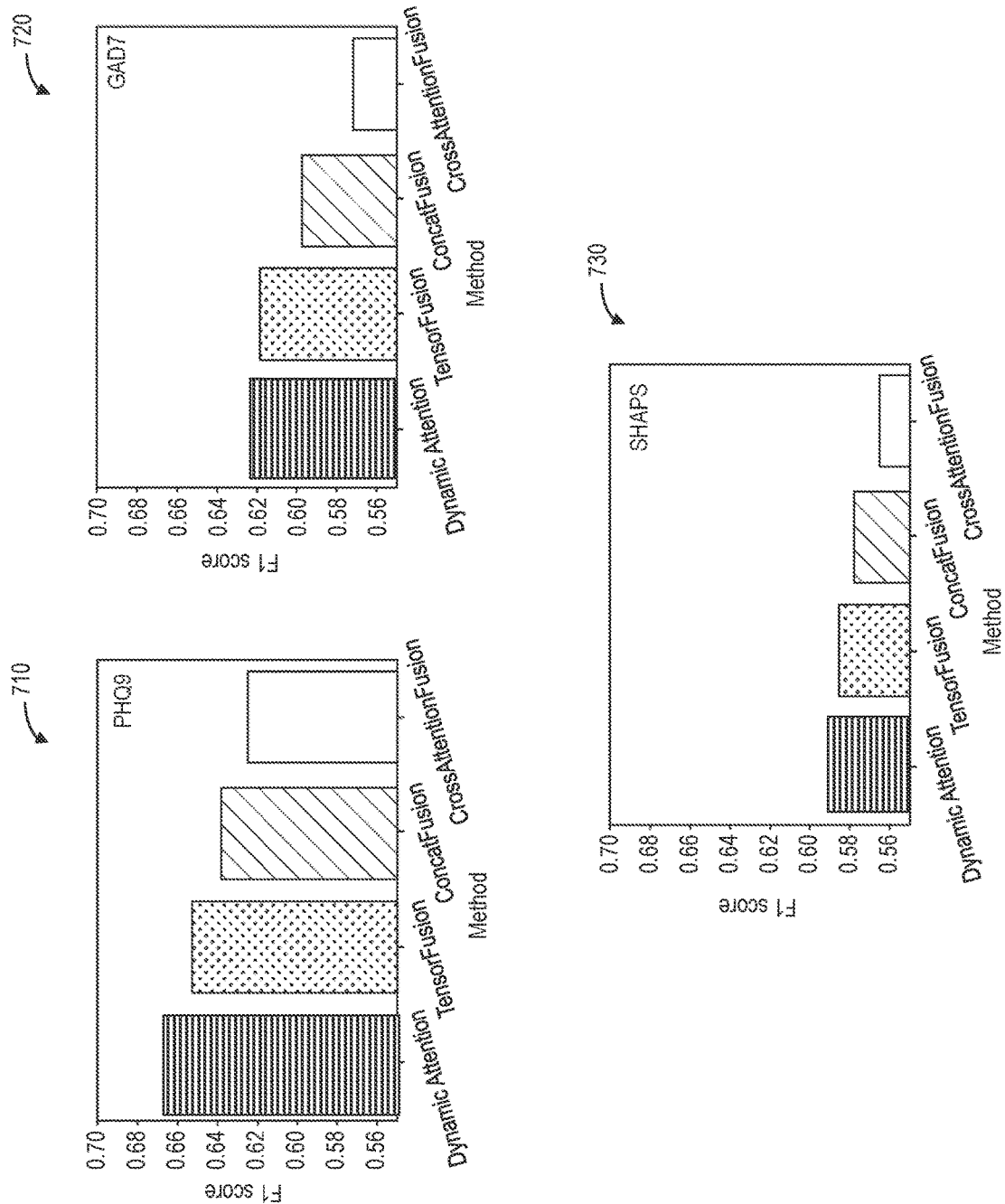
FIG. 7 depicts graphs showing comparison of performance of the trained dynamic fusion model with other models.

(1) The overall classification performance across the three scales (using median test F1 score as the metric) were compared and shown in Table 1 below. The dynamic fusion method performed better compared to the other methods across the three scales; it outperformed the next best model (i.e. LSTM-Tensor Fusion) by 4.94%, 3.60% and 3.98% for PHQ-9, GAD-7 and SHAPS respectively. FIG. 7 also shows comparison of multimodal dynamic fusion performance with respect to previous models. In particular, FIG. 7 shows bar graphs depicting performance of different models for depression, anxiety, and anhedonia classifications at 710, 720, and 730 respectively. The performance is shown for depression classification (PHQ-9), anxiety classification (GAD-7), and Anhedonia classification (SHAPS).

TABLE 1

Multimodal classification of mood disorder symptoms: Median Test F1 Score

| Fusion Approach | PHQ-9 | GAD-7 | SHAPS |
|---|---|---|---|
| LSTM-Concatenation | 0.638 | 0.598 | 0.578 |
| BiLSTM-Static Attention | 0.625 | 0.5716 | 0.566 |
| LSTM-Tensor Fusion | 0.632 | 0.601 | 0.567 |
| CNN-Dynamic Attention | 0.664 | 0.623 | 0.590 |

(2) Models with each of the modalities were built and the performance of the multimodal model vs the best unimodal model (using the percentage difference in median test F1 score between multimodal and best unimodal) was compared for the different approaches and across the three scales (Table 2 below). The dynamic fusion method showed a notable increase in performance in the multimodal case whereas the other approaches showed very minor increase (or sometimes decrease). This demonstrated that the dynamic fusion method was able to efficiently capture the supplementary information across different modalities.

TABLE 2

Percentage Difference in Median Test F1 Score between trimodal and best unimodal model

| Scale | Approach | Percentage Difference |
|---|---|---|
| PHQ-9 | LSTM-Concatenation | −0.79 |
|  | BiLSTM-Static Attention | 0 |
|  | LSTM-Tensor Fusion | 0.16 |
|  | CNN-Dynamic Attention | 3.05 |
| GAD-7 | LSTM-Concatenation | −2.68 |
|  | BiLSTM-Static Attention | −0.84 |
|  | LSTM-Tensor Fusion | 0.16 |
|  | CNN-Dynamic Attention | 2.27 |
| SHAPS | LSTM-Concatenation | −1.77 |
|  | BiLSTM-Static Attention | 0.17 |
|  | LSTM-Tensor Fusion | 0 |
|  | CNN-Dynamic Attention | 1.88 |

Figure 8:
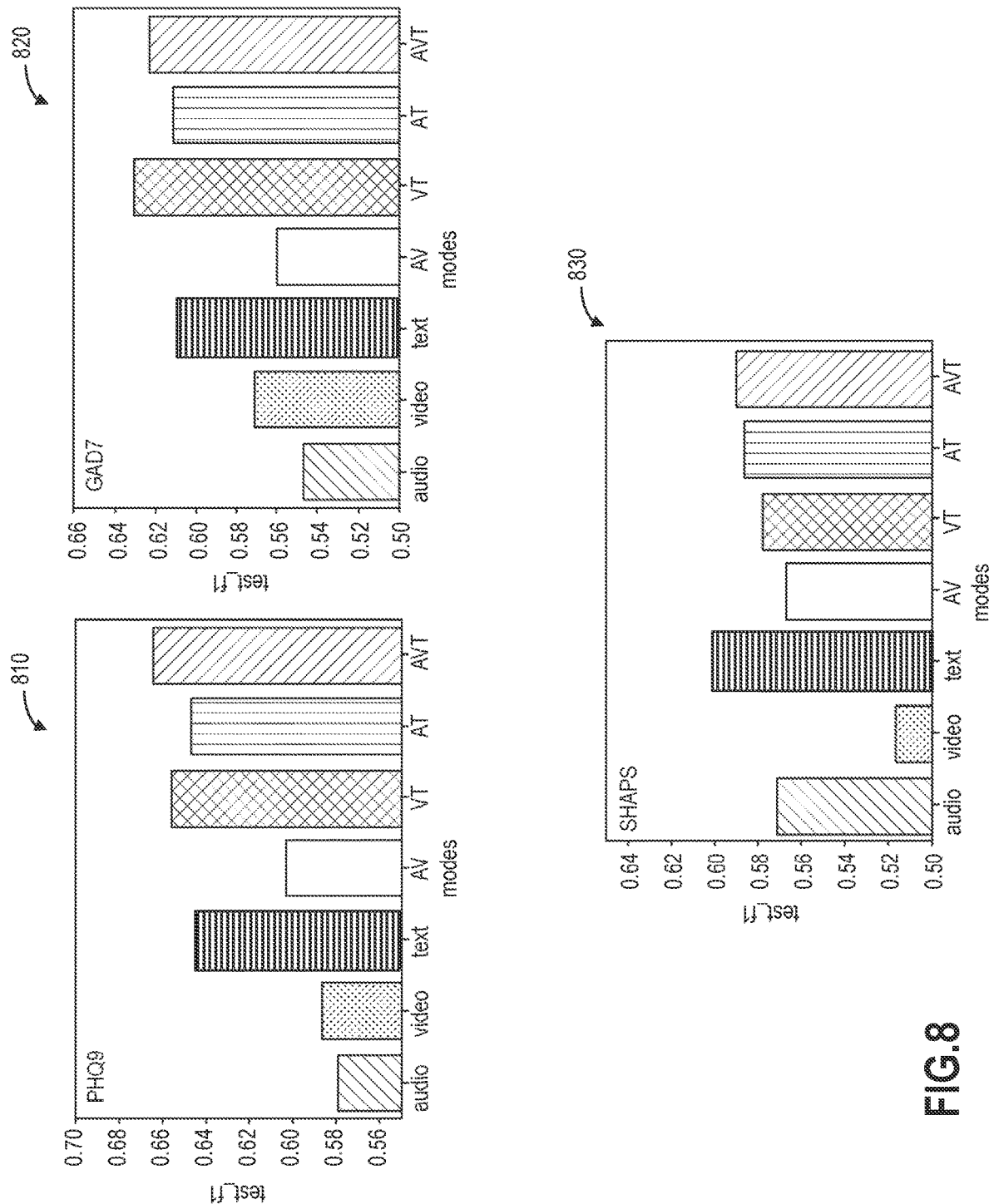
FIG. 8 depicts graphs showing F1 scores for prediction across unimodal, bimodal, and trimodal evaluations with the trained dynamic fusion model.

As indicated above, models for each modality (audio, video and text) were built and trained and the performance of the best performing unimodal was compared with the multimodal model for each approach and scale. The complete results are shown in table 3 below and FIG. 8. FIG. 8 shows bar graphs depicting performance of unimodal and trimodal models for depression, anxiety, and anhedonia classifications at 810, 820, and 830 respectively. To train models with only one modality, after learning the dynamic unimodal embedding using the 1D-CNN based unimodal Encoder, the output was flattened through max and mean pooling, these two vectors were concatenated and input to a fully-connected layer (with dropout) followed by softmax activation to generate the output probability and trained using backpropagation.

TABLE 3

Comparison between median test F1 scores for unimodal vs trimodal models

| Scale | Approach | Audio Performance | Video Performance | Text Performance | Trimodal Performance | Percentage Difference between Multimodal & Best Unimodal Model |
|---|---|---|---|---|---|---|
| PHQ-9 | LSTM-Concatenation | 0.566 | 0.568 | 0.633 | 0.628 | −0.79 |
|  | BiLSTM-Static Attention | 0.565 | 0.572 | 0.629 | 0.629 | 0 |
|  | LSTM-Tensor Fusion | 0.548 | 0.559 | 0.632 | 0.633 | 0.16 |
|  | CNN-Dynamic Attention | 0.579 | 0.587 | 0.644 | 0.664 | 3.05 |
| GAD-7 | LSTM-Concatenation | 0.544 | 0.560 | 0.604 | 0.588 | −2.68 |
|  | BiLSTM-Static Attention | 0.546 | 0.572 | 0.600 | 0.595 | −0.84 |
|  | LSTM-Tensor Fusion | 0.552 | 0.564 | 0.600 | 0.601 | 0.16 |
|  | CNN-Dynamic Attention | 0.547 | 0.570 | 0.609 | 0.623 | 2.27 |
| SHAPS | LSTM-Concatenation | 0.536 | 0.518 | 0.567 | 0.557 | −1.77 |
|  | BiLSTM-Static Attention | 0.544 | 0.519 | 0.564 | 0.565 | 0.17 |
|  | LSTM-Tensor Fusion | 0.541 | 0.517 | 0.567 | 0.567 | 0 |
|  | CNN-Dynamic Attention | 0.571 | 0.517 | 0.579 | 0.590 | 1.88 |

Feature Importance

Figure 9A:
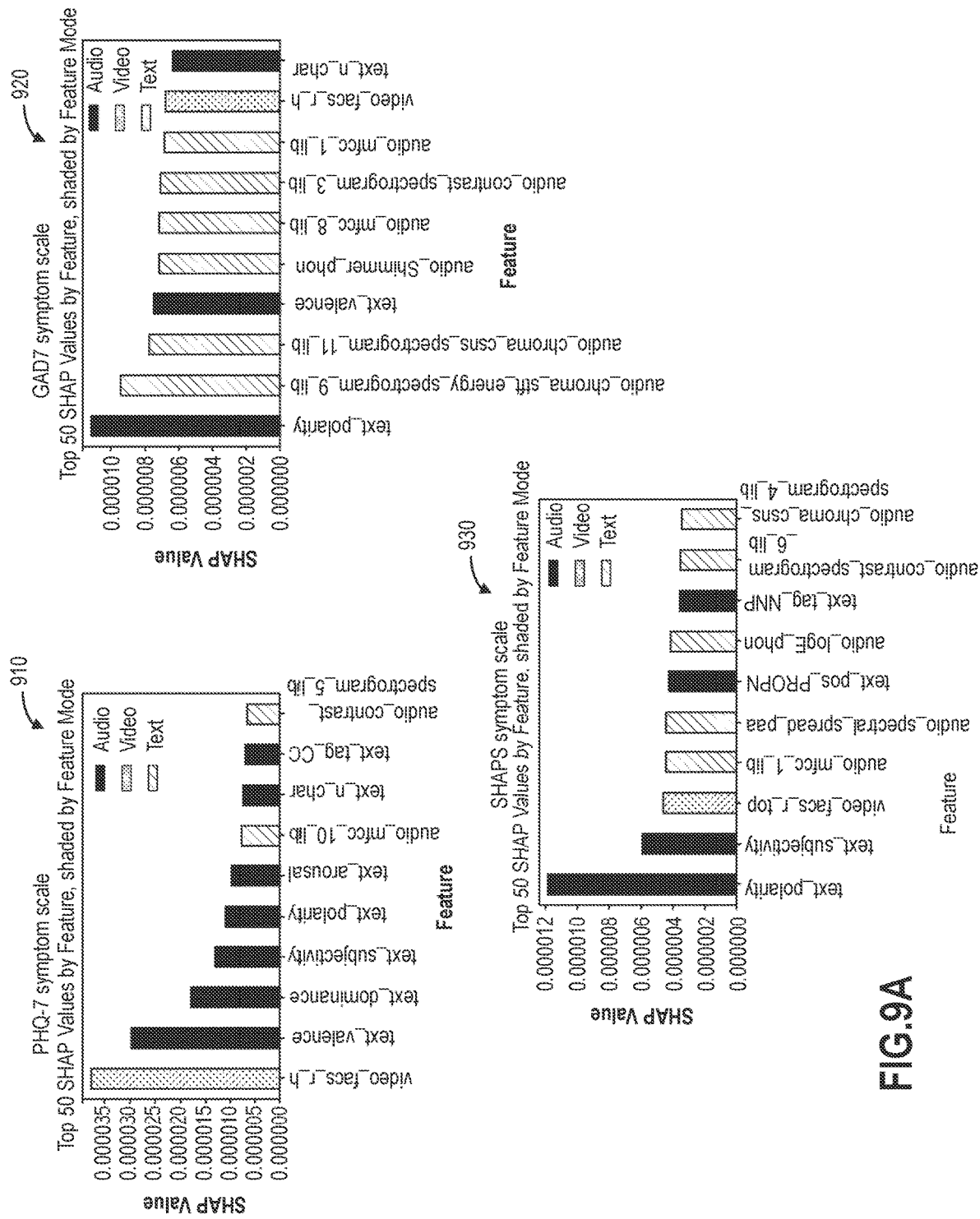
FIG. 9A depicts graphs showing SHapley Additive exPlanations (SHAP) values for a plurality of features.

Next, SHAP scores were computed for the input features, ranked by scores, and then used the top 5, 10, 25, 50 and 75% features for secondary modeling (Table 4 below and FIG. 9A). FIG. 9A shows bar graphs depicting top SHAP values for depression, anxiety, and anhedonia symptom scales at 910, 920, and 930 respectively. Model performance remained fairly stable even at low number of features. For example, for each scale, models built using only 25% of the original set of features achieved test F1 scores within 3% of the models built using all features. Specifically, for PHQ-9, the difference between the highest F1 (with 75% of features) and the lowest (with 5% of features) was only 1%. These results suggest that a low number of features contributed heavily to the model performance and shows that the SHAP method can effectively identify them.

TABLE 4

Multimodal classification using reduced number of features selected by SHAP scores: Median Test F1 Score

| % of total features used | PHQ-9 | GAD-7 | SHAPS |
|---|---|---|---|
| 5 | 0.657 | 0.542 | 0.563 |
| 10 | 0.654 | 0.588 | 0.580 |
| 25 | 0.656 | 0.620 | 0.575 |
| 50 | 0.661 | 0.638 | 0.595 |
| 75 | 0.667 | 0.628 | 0.599 |
| 100 | 0.664 | 0.623 | 0.590 |

Despite differences in the number of features for each modality, the top 10 SHAP-identified most important features for each scale had representation from each modality (Table in FIG. 9B). Several features co-occurred across multiple disorders including text features like Polarity, Subjectivity, Valence and Number of characters and video features including Facial Action Units concerning lip movement. Additionally, there were related audio features that co-occurred across multiple disorders viz. spectral features (Contrast Spectrogram, MFCC and Chroma Energy Normalized Spectrogram) and phonation features (Shimmer and Logarithimic Energy). However, several features were specific to mood disorders e.g. affective text features (Arousal Dominance) for PHQ-9 and Noun tags for SHAPS. These results highlight some of the shared and divergent themes of these different mood disorders.

The SHAP based interpretability method enabled the computation of the SHAP values for all the input features (which are time series features) over each point of time. For examples, clinicians could use these type of data to isolate the impacts of specific words, facial or vocal expressions, or to find particularly salient portions of the video in larger clips. As an example, the time series SHAP values of one participant for the top audio, video and text features for each of the scales is shown in FIG. 10. Referring to FIG. 10, it shows a graph 1010 for depression scale (PHQ-9) for a subject, a graph 1020 for anxiety scale (GAD-7), and a graph 1030 for anhedonia scale (SHAPS). The graphs 1010, 1020, and 1020 show SHAP values along Y-axis and time along x-axis. Further, each of the graphs show audio features in plot 1012, video features in plot 1014, and text features in plot 1016. The top features in each modality may be identified based on the plots of SHAP values over time. Specific segments along the time series that are of high importance may be identified over time. Further the specific segments along the time series may be selected and corresponding video clip of the subject may be determined and output via a user interface. In some examples, a first evaluation and a first interpretation output, including one or more graphs for each mental health evaluation scale, such as the graphs at FIG. 10, may be generated. The first interpretation output may serve as a baseline for monitoring effect of treatment, progression of the mental health condition, change in ration of depression/anxiety/anhedonia in a patient over time, etc.

In this way, a novel, interpretable, multimodal classification method is provided to identify the symptoms of depression, anxiety and anhedonia using audio, video and text data collected from a smartphone app. An advancement of the multimodal dynamic fusion framework involved using dynamic (i.e. temporal) embeddings for individual modalities and then fusing these using a transformer encoder. This strategy outperformed prior state-of-the-art methods that rely on static (i.e. non-temporal) embeddings in overall F1 scores as well as capturing supplementary multimodal information. Lastly, a SHAP-based method was used to recover the small number of multimodal features that had outsized contributions to the models for validation and digital marker discovery. These analyses were performed on data collected from smartphones outside of clinical/laboratory settings, and further required extensive quality control procedures (which could be incorporated into the design and implementation of remote studies).

In one example, the generalization of these models could be confirmed in independent cohort(s), and the identified features could be validated using a V3 framework. Additionally, in some examples, age and gender may be integrated in models, which may improve generalizability.

In one embodiment, a device comprises a modality processing logic to process data output from at least two types of sensors to output a set of data representations for each of the at least two types of sensors, wherein each of the set of data representations comprising a vector comprising a set of features; modality combination logic to process the set of data representation to output a combined data representation; diagnosis determination logic to determine a health diagnosis based on the relevance of the combined data representation to a mental health diagnosis; and a feature relevance determination logic to process the mental health diagnosis and determine a relevance of each of the set of features to the mental health diagnose. In one example of the device, the feature relevance determination logic is a SHAP model. In a second example of the device which optionally includes the first example, the device further comprising a feature relevance display logic to display a portion of the data recorded by the camera or microphone comprising features of the set of features with a relevance over a threshold relevance. In a third example of the device which includes one or more of the first and second examples, the device further comprising highlighting one or more selected features, the one or more selected features having a relevance threshold greater than a threshold relevance. In a fourth example of the device which includes one or more of the first through third examples, the set of features comprise the features listed in FIG. 9B. In a fifth example of the device which includes one or more of the first through fourth examples, the set of data representations are generated using a convolutional neural network. In a sixth example of the device which includes one or more of the first through fifth examples, the convolutional neural network is a one dimensional convolutional neural network. In a seventh example of the device which includes one or more of the first through sixth examples, the set of data representations include a set of embeddings, each comprising timing information from data output from the at least two sensors. In an eighth example of the device which includes one or more of the first through seventh examples, the modality combination logic comprises one or more transformer encoders. In a ninth example of the device which includes one or more of the first through eighth examples, the timing information comprises a time stamp added by a timing synchronization logic to synchronize the time stamps across features and sensors. In a tenth example of the device which includes one or more of the first through ninth examples, the mental health diagnosis comprises at least one of: a psychiatric disorder, a depression, a schizophrenia, an anxiety, a panic disorder, a borderline personality disorder, an obsessive compulsive disorder, a post-traumatic stress disorder, an autism spectrum disorder, a mood disorder in epilepsy, a personality disorder, a cognitive change associated with chemotherapy, an attention deficit hyperactivity disorder (ADHD), a neurodevelopmental disorder, a neurodegenerative disorder, an Alzheimer's disease, or a dementia.

In another embodiment, a device may comprise a modality processing logic to process data output from at least two types of sensors to output a set of data representations for each of the at least two types of sensors, wherein each of the set of data representations comprising a set of embeddings, the set of embeddings including timing information for each data representation; a modality combination logic to process the set of data representation to output a combined data representation, the combined data representation including the timing information; and a diagnosis determination logic to determine a health diagnosis based on the relevance of the combined data representation to a health diagnosis. In a first example of the device, process data output from the at least two types of sensors comprises process data captured simultaneously by the at least two types of sensors. In a second example of the device which optionally includes the first example, the at least two types of sensors are a microphone and a camera. In a third example of the device which includes one or more of the first and second examples, the set of data representations are generated using a convolutional neural network. In a fourth example of the device, which includes one or more of the first through third examples, the convolutional neural network is a one dimensional convolutional neural network. In a fifth example of the device, which includes one or more of the first through fourth examples, process data output from at the least two types of sensors comprises extracting a set of features from data output from each of the at least two types of sensors, the set of features including timing information for each of the set of extracted features. In a sixth example of the device, which includes one or more of the first through fifth examples, the modality combination logic comprises one or more transformer encoders. In a seventh example of the device, which includes one or more of the first through fifth examples, process the set of data representation to output a combined data representation is based on a self-attention mechanism or a multi-head attention mechanism. In an eighth example of the device, which includes one or more of the first through seventh examples, the diagnosis determination logic comprises a supervised machine learning model. In a ninth example of the device, which includes one or more of the first through eighth examples, the supervised machine learning model comprises a random forest, support vector machine, Bayesian Decision List, linear regression, logistic regression, naïve Bayes, linear discriminant analysis, decision tree, k-nearest neighbor, or neural network. In a tenth example of the device, which includes one or more of the first through ninth examples, the supervised machine learning model is trained using responses to clinical questionnaires as the outcome label. In an eleventh example of the device, which includes one or more of the first through tenth examples, the camera is a three dimensional camera. In a twelfth example of the device, which includes one or more of the first through eleventh examples, the mental health diagnosis comprises at least one of: a psychiatric disorder, a depression, a schizophrenia, an anxiety, a panic disorder, a borderline personality disorder, an obsessive compulsive disorder, a post-traumatic stress disorder, an autism spectrum disorder, a mood disorder in epilepsy, a personality disorder, a cognitive change associated with chemotherapy, an attention deficit hyperactivity disorder (ADHD), a neurodevelopmental disorder, a neurodegenerative disorder, an Alzheimer's disease, or a dementia. In a thirteenth example of the device, which includes one or more of the first through twelfth examples, the mental health diagnosis comprises a quantitative assessment of a severity of the mental health disorder. In a fourteenth example of the device, which includes one or more of the first through thirteenth examples, the set of representations include three-dimensional facial landmarks. In a fifteenth example of the device, which includes one or more of the first through fourteenth examples, the timing information comprises a time stamp added by a timing synchronization logic to synchronize the time stamps across features and sensors.

Selected Embodiments

Although the above description and the attached claims disclose a number of embodiments of the present invention, other alternative aspects of the invention are disclosed in the following further embodiments.

Embodiment 1: A device comprising: a modality processing logic to process data output from at least two types of sensors to learn a set of dynamic data representations for each of the at least two types of sensors, wherein each of the set of dynamic data representations comprising a vector comprising a set of features; a modality combination logic to process the set of dynamic data representation to learn a combined dynamic data representation; diagnosis determination logic to determine a health diagnosis based on the relevance of the combined data representation to a mental health diagnosis; and a model explanation logic to process the mental health diagnosis and determine a relevance of each of the set of features to the mental health diagnosis.

Embodiment 2. The device of embodiment 1, wherein the model explanation logic is a SHAP model.

Embodiment 3. The device of embodiment 1, further comprising a model explanation display logic to display a portion of the data recorded by the camera or microphone comprising features of the set of features with a relevance over a threshold relevance.

Embodiment 4. The device of embodiment 1, further comprising highlighting one or more selected features, the one or more selected features having a relevance threshold greater than a threshold relevance.

Embodiment 5. The device of embodiment 1, wherein the set of features comprise one or more features important to diagnosis of one or more of depression, general anxiety disorder, and anhedonia, the one or more features, each independently selected from the group consisting of: lower lip depressor, valence, dominance, subjectivity polarity, arousal, MFCC 10, number of characters, coordinating conjunction tag, contrast spectrogram 5, polarity, Short-Time fourier transform energy spectrogram 9, chroma energy normalized spectrogram 11, shimmer, MFCC 8, contrast spectrogram MFCC 1, upper lip raiser, MFCC1 spectral spread, proper noun tag, logarithmic energy, singular noun tag, contrast spectrogram 6, and chroma energy normalized spectrogram 4.

Embodiment 6. The device of embodiment 1, wherein the set of data representations are generated using a convolutional neural network.

Embodiment 7. The device of embodiment 6, wherein the convolutional neural network is a one dimensional convolutional neural network.

Embodiment 8. The device of embodiment 1, wherein the set of data representations include a set of embeddings, each comprising timing information from data output from the at least two sensors.

Embodiment 9. The device of embodiment 1, wherein the modality combination logic comprises one or more transformer encoders.

Embodiment 10. The device of embodiment 8, wherein the timing information comprises a time stamp added by a timing synchronization logic to synchronize the time stamps across features and sensors.

Embodiment 11. The device of embodiment 1, wherein the mental health diagnosis comprises at least one of: a psychiatric disorder, a depression, a schizophrenia, an anxiety, a panic disorder, a borderline personality disorder, an obsessive compulsive disorder, a post-traumatic stress disorder, an autism spectrum disorder, a mood disorder in epilepsy, a personality disorder, a cognitive change associated with chemotherapy, an attention deficient hyperactivity disorder (ADHD), a neurodevelopmental disorder, a neurodegenerative disorder, an Alzheimer's disease, or a dementia.

Embodiment 12. A device comprising: a modality processing logic to process data output from at least two types of sensors to output a set of dynamic data representations for each of the at least two types of sensors, wherein each of the set of dynamic data representations comprising a vector comprising a set of features; a modality combination logic to process each of the set of dynamic data representation to output a combined data representation; a diagnosis determination logic to determine a health diagnosis based on a relevance of the combined data representation to a mental health diagnosis; a model explanation generator logic to identify importance of the sets of dynamic data representations to a health diagnosis; wherein the model explanation logic is based on a subset of the set of features determined by a feature relevance determination logic processing a previously determined mental health diagnosis based on a second modality processing logic and the set of features.

Embodiment 13. The device of embodiment 12, wherein the subset includes one or more features, each independently selected from the group consisting of: lower lip depressor, valence, dominance, subjectivity polarity, arousal, MFCC 10, number of characters, coordinating conjunction tag, contrast spectrogram 5, polarity, Short-Time fourier transform energy spectrogram 9, chroma energy normalized spectrogram 11, shimmer, MFCC 8, contrast spectrogram 3, MFCC 1, upper lip raiser, MFCC1 spectral spread, proper noun tag, logarithmic energy, singular noun tag, contrast spectrogram 6, and chroma energy normalized spectrogram 4.

Embodiment 14. The device of embodiment 12, further comprising a display having a user interface to display an indication of the subset of the set of features, and responsive to selection of a portion of the subset of the set of features or selection of the subset of the set of the features, automatically rendering a corresponding portion of the data output from the sensors.

Embodiment 15. The device of claim 12, further comprising a display having a user interface to display the subset of the set of features and automatically rendering the subset of set of features, wherein the subset of set of features has a relevance score greater than a threshold relevance.

Embodiment 16. A device, comprising: a modality processing logic to process time series data, the time series data output from at least two types of sensors, to output a set of data representations for each of the at least two types of sensors, wherein each of the set of data representations comprising a set of dynamic embeddings, the set of dynamic embeddings including timing information for each data representation; a modality combination logic to process the set of data representation to output a combined dynamic data representation, the combined dynamic data representation including the timing information; and a diagnosis determination logic to determine a mental health diagnosis based on a relevance of the combined data representation to a mental health diagnosis.

Embodiment 17. The device of claim 16, wherein process data output from the at least two types of sensors comprises process data captured simultaneously by at the least two types of sensors.

Embodiment 18. The device of claim 16, wherein the at least two types of sensors are a microphone and a camera.

Embodiment 19. The device of claim 16, wherein the set of data representations are generated using a convolutional neural network.

Embodiment 20. The device of claim 19, wherein the convolutional neural network is a one dimensional convolutional neural network.

Embodiment 21. The device of claim 16, wherein process data output from at the least two types of sensors comprises extracting a set of features from data output from each of the at least two types of sensors, the set of features including timing information for each of the set of extracted features.

Embodiment 22. The device of claim 16, wherein the modality combination logic comprises one or more transformer encoders.

Embodiment 23. The device of claim 22, process the set of data representation to output a combined data representation is based on a self-attention mechanism or a multi-head attention mechanism.

Embodiment 24. The device of claim 16, wherein the diagnosis determination logic comprises a supervised machine learning model.

Embodiment 25. The device of claim 24, wherein the supervised machine learning model comprises a random forest, support vector machine, Bayesian Decision List, linear regression, logistic regression, naïve Bayes, linear discriminant analysis, decision tree, k-nearest neighbor, or neural network.

Embodiment 26. The device of claim 24, wherein the supervised machine learning model is trained using responses to clinical questionnaires as the outcome label.

Embodiment 27. The device of claim 18, wherein the camera is a three dimensional camera.

Embodiment 28. The device of claim 16, wherein the mental health diagnosis comprises at least one of: a psychiatric disorder, a depression, a schizophrenia, an anxiety, a panic disorder, a borderline personality disorder, an obsessive compulsive disorder, a post-traumatic stress disorder, an autism spectrum disorder, a mood disorder in epilepsy, a personality disorder, a cognitive change associated with chemotherapy, an attention deficit hyperactivity disorder (ADHD), a neurodevelopmental disorder, a neurodegenerative disorder, an Alzheimer's disease, or a dementia.

Embodiment 29. The device of claim 16, wherein the mental health diagnosis comprises a quantitative assessment of a severity of the mental health disorder.

Embodiment 30. The device of claim 16, wherein the set of representations include three-dimensional facial landmarks.

Embodiment 31. The device of claim 21, wherein the timing information comprises a time stamp added by a timing synchronization logic to synchronize the time stamps across features and sensors.

Embodiment 32. A computing device comprising: a memory comprising machine executable code having stored thereon instructions; and a control system coupled to the memory, the control system comprising one or more processors and configured to execute the machine executable code to cause the control system to: receive, a plurality of time-series datasets from a plurality of devices; process, each of the plurality of time-series datasets, via respective unimodal encoders, to learn dynamic embeddings corresponding to each time-series dataset; and combine the plurality of dynamic embeddings with a modality combination model to learn a combined set of multimodal dynamic embeddings; and process the set of multimodal dynamic embeddings using one or more supervised trained models to output one or more mental health diagnoses.

Embodiment 33. The computing device of claim 32, wherein the modality combination model is a dynamic attention-based model including one or more transformer encoders.

Embodiment 34. The computing device of claim 32, wherein the each of the plurality of dynamic embeddings include timing information from each of the plurality of devices respectively; and wherein the combined set of dynamic embedding includes timing information from the plurality of devices.

Embodiment 35. The computing device of claim 32, wherein the one or more mental health diagnoses includes diagnosis of one or more mental health conditions, the one or more mental health conditions wherein the one or more mental health conditions include one or more of a psychiatric disorder, a depression, a schizophrenia, an anxiety, a panic disorder, a borderline personality disorder, an obsessive compulsive disorder, a post-traumatic stress disorder, an autism spectrum disorder, a mood disorder in epilepsy, a personality disorder, a cognitive change associated with chemotherapy, ADHD, a neurodevelopmental disorder, a neurodegenerative disorder, an Alzheimer's disease, and a dementia.

Embodiment 36. The computing device of claim 32, wherein the plurality of devices include one or more of an audio sensor, a video camera, and a text generator.

Embodiment 37. The computing device of claim 32, wherein each of the unimodal encoders are trained to learn respective dynamic embeddings, and wherein each of the unimodal encoders include one or more one dimensional convolutional layers.

Embodiment 38. A computing device comprising: a memory comprising machine executable code having stored thereon instructions; and a control system coupled to the memory, the control system comprising one or more processors and configured to execute the machine executable code to cause the control system to: receive, a first time series data acquired via a first device, a second time series data acquired via a second device, and a third time series data acquired via a third device; process the first, the second, and the third time series data via respective unimodal encoders to learn a first dynamic embedding, a second dynamic embedding, and a third dynamic embedding; combine the first dynamic embedding, the second dynamic embedding, and the third dynamic embedding to generate a combined multimodal dynamic embedding; diagnose one or more mental health conditions based on the combined multimodal dynamic embedding; wherein the first, the second, and the third dynamic embeddings include respective timing information in the first, the second, and the third time series data respectively; and wherein the combined multimodal dynamic embedding includes timing information in the first, the second, and the third time series data respectively.

Embodiment 39. The device of claim 38, wherein the first, the second, and the third time-series data are preprocessed to extract a first set of features, a second set of features, and a third set of features respectively, prior to inputting into the respective unimodal encoders.

Embodiment 40. The device of claim 38, wherein each unimodal encoder comprises one or more one dimensional convolutional layers.

Embodiment 41. The device of claim 38, wherein the first dynamic embedding, the second dynamic embedding, and the third dynamic embedding are processed using one or more transformer encoders to generate the combined multimodal dynamic embedding.

Embodiment 42. The device of claim 38, wherein each transformer encoder comprises a plurality of multi-head attention heads.

Embodiment 43. The device of claim 38, wherein the one or more mental health conditions include one or more of a depressive disorder, an anxiety disorder, and an anhedonic condition Embodiment 44. The method of claim 38, wherein the first, the second, and the third time series data are synchronized in time.

Embodiment 45. The method of claim 38, wherein the first device is an audio sensor, the second device is a video camera, and the third device is a speech-to-text generator.

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

Computer & Hardware Implementation of Disclosure

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a "control system" on data stored on one or more computer-readable storage devices or received from other sources.

The term "control system" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

Conclusion

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

The invention claimed is:
1. A device, comprising:
a memory coupled to a control system, the control system comprising:
a modality processing logic to process time series data, the time series data output from at least two types of sensors and pre-processed to a common timing resolution, to output a set of data representations for each of the at least two types of sensors, each of the set of data representations comprising a set of dynamic embeddings, the set of dynamic embeddings including timing information for each data representation;

a modality combination logic to process the set of data representation via a plurality of unimodal encoders to output a combined dynamic data representation, the combined dynamic data representation including the timing information, the modality combination logic comprising one or more transformer encoders and one or more positional encoders, the one or more transformer encoders taking as an input the set of data representations positionally encoded using the one or more positional encoders; and a diagnosis determination logic including a supervised machine learning model trained using a dataset of time series data relating to mood disorder symptoms collected from users and a set of corresponding outcome labels of mental health conditions, the modality combination logic to determine a mental health diagnosis based on a relevance of the combined dynamic data representation to a mental health diagnosis.

2. The device of claim 1, wherein process data output from the at least two types of sensors comprises process data captured simultaneously by the at least two types of sensors.

3. The device of claim 1, wherein the at least two types of sensors are a microphone and a camera.

4. The device of claim 1, wherein the modality processing logic includes a convolutional neural network that generates the set of data representations.

5. The device of claim 4, wherein the convolutional neural network is a one dimensional convolutional neural network.

6. The device of claim 1, wherein process data output from at the least two types of sensors comprises extracting a set of features from data output from each of the at least two types of sensors, the set of features including timing information for each of the set of extracted features.

7. The device of claim 1, wherein the combined dynamic data representation is generated further using a self-attention mechanism or a multi-head attention mechanism.

8. The device of claim 1, wherein the supervised machine learning model comprises a random forest, support vector machine, Bayesian Decision List, linear regression, logistic regression, naïve Bayes, linear discriminant analysis, decision tree, k-nearest neighbor, or neural network.

9. The device of claim 1, wherein the supervised machine learning model is trained using responses to clinical questionnaires as the outcome labels.

10. The device of claim 3, wherein the camera is a three dimensional camera.

11. The device of claim 1, wherein the mental health diagnosis comprises at least one of: a psychiatric disorder, a depression, a schizophrenia, an anxiety, a panic disorder, a borderline personality disorder, an obsessive compulsive disorder, a post-traumatic stress disorder, an autism spectrum disorder, a mood disorder in epilepsy, a personality disorder, a cognitive change associated with chemotherapy, an attention deficit hyperactivity disorder (ADHD), a neurodevelopmental disorder, a neurodegenerative disorder, an Alzheimer's disease, or a dementia.

12. The device of claim 1, wherein the mental health diagnosis comprises a quantitative assessment of a severity of the mental health disorder.

13. The device of claim 1, wherein the set of representations include three-dimensional facial landmarks.

14. The device of claim 6, wherein the timing information comprises a time stamp added by a timing synchronization logic to synchronize the time stamps across features and sensors.

15. A computing device comprising:
a memory comprising machine executable code having stored thereon instructions; and
a control system coupled to the memory, the control system comprising one or more processors and configured to execute the machine executable code to cause the control system to:
receive plurality of time-series datasets from a plurality of devices;
pre-process the plurality of time-series datasets to a common timing resolution;
process the plurality of time-series datasets via a plurality of unimodal encoders to learn dynamic embeddings corresponding to each time-series dataset;
combine the plurality of dynamic embeddings with a modality combination model to learn a combined set of multimodal dynamic embeddings, the modality combination model including one or more transformer encoders and one or more positional encoders, the one or more transformer encoders taking as an input the set of time-series datasets positionally encoded using the one or more positional encoders; and
determine a mental health diagnosis based on processing the set of multimodal dynamic embeddings using one or more supervised trained models to output one or more mental health diagnoses, wherein the one or more supervised training models are trained using a dataset of time series data relating to mood disorder symptoms collected from users and a set of corresponding outcome labels of mental health conditions.

16. The computing device of claim 15, wherein the each of the plurality of dynamic embeddings include timing information from each of the plurality of devices respectively; and wherein the combined set of dynamic embedding includes timing information from the plurality of devices.

17. The computing device of claim 15, wherein the one or more mental health diagnoses includes diagnosis of one or more mental health conditions, the one or more mental health conditions wherein the one or more mental health conditions include one or more of a psychiatric disorder, a depression, a schizophrenia, an anxiety, a panic disorder, a borderline personality disorder, an obsessive compulsive disorder, a post-traumatic stress disorder, an autism spectrum disorder, a mood disorder in epilepsy, a personality disorder, a cognitive change associated with chemotherapy, ADHD, a neurodevelopmental disorder, a neurodegenerative disorder, an Alzheimer's disease, and a dementia.

18. The computing device of claim 15, wherein the plurality of devices include one or more of an audio sensor, a video camera, and a text generator.

19. The computing device of claim 15, wherein each of the unimodal encoders are trained to learn respective dynamic embeddings, and wherein each of the unimodal encoders include one or more one dimensional convolutional layers.

20. A computing device comprising:
a memory comprising machine executable code having stored thereon instructions; and
a control system coupled to the memory, the control system comprising one or more processors and configured to execute the machine executable code to cause the control system to:
receive, a first time series data acquired via a first device, a second time series data acquired via a second device, and a third time series data acquired via a third device;
pre-process one or more of the first, the second, and the third time series to a common timing resolution;

process the first, the second, and the third time series data via respective unimodal encoders to learn a first dynamic embedding, a second dynamic embedding, and a third dynamic embedding;

combine the first dynamic embedding, the second dynamic embedding, and the third dynamic embedding to generate a combined multimodal dynamic embedding, wherein the combined multimodal dynamic embedding is generated using one or more position-encoding transformer encoders and one or more positional encoders, the one or more transformer encoders taking as an input the set of multimodal dynamic embedding positionally encoded using the one or more positional encoders;

diagnose one or more mental health conditions based on the combined multimodal dynamic embedding, via executing a supervised machine learning model trained using a dataset of time series data relating to mood disorder symptoms collected from users and a set of corresponding outcome labels of mental health conditions;

wherein the first, the second, and the third dynamic embeddings include respective timing information in the first, the second, and the third time series data respectively; and wherein the combined multimodal dynamic embedding includes timing information in the first, the second, and the third time series data respectively.

21. The device of claim 20, wherein the first, the second, and the third time-series data are further pre-processed to extract a first set of features, a second set of features, and a third set of features respectively, prior to inputting into the respective unimodal encoders.

22. The device of claim 20, wherein each unimodal encoder comprises one or more one dimensional convolutional layers.

23. The device of claim 20, wherein each transformer encoder comprises a plurality of multi-head attention heads.

24. The device of claim 20, wherein the one or more mental health conditions include one or more of a depressive disorder, an anxiety disorder, and an anhedonia condition.

25. The device of claim 20, wherein the first, the second, and the third time series data are synchronized in time.

26. The device of claim 20, wherein the first device is an audio sensor, the second device is a video camera, and the third device is a speech-to-text generator.

* * * * *